(12) United States Patent
Brodsky et al.

(10) Patent No.: US 9,279,803 B2
(45) Date of Patent: Mar. 8, 2016

(54) METHOD OF IDENTIFYING PATIENTS NOT SUITABLE FOR HIGH-DOSE CYCLOPHOSPHAMIDE TREATMENT

(75) Inventors: Robert A. Brodsky, Brooklandville, MD (US); Richard J. Jones, Baltimore, MD (US); Francis E. O'Donnell, Jr., Longboat Key, FL (US); Susan Bonitz, Flemington, NJ (US); Adam Kaplin, Baltimore, MD (US); Carlos Santos, Tampa, FL (US)

(73) Assignees: The Johns Hopkins University, Baltimore, MD (US); Accentia Biopharmaceuticals, Inc., Tampa, FL (US)

( * ) Notice: Subject to any disclaimer, the term of this patent is extended or adjusted under 35 U.S.C. 154(b) by 299 days.

(21) Appl. No.: 13/240,443

(22) Filed: Sep. 22, 2011

(65) Prior Publication Data

US 2012/0129206 A1    May 24, 2012

Related U.S. Application Data

(63) Continuation of application No. 13/026,590, filed on Feb. 14, 2011, now abandoned, which is a continuation of application No. 12/827,773, filed on Jun. 30, 2010, now abandoned, which is a continuation of application No. 12/610,756, filed on Nov. 2, 2009, now abandoned, which is a continuation of application No. 12/404,900, filed on Mar. 16, 2009, now abandoned, which is a continuation of application No. PCT/US2007/078518, filed on Sep. 14, 2007.

(60) Provisional application No. 60/844,829, filed on Sep. 15, 2006.

(51) Int. Cl.
G01N 33/50    (2006.01)
G01N 33/94    (2006.01)
C12Q 1/32     (2006.01)

(52) U.S. Cl.
CPC ............ *G01N 33/5047* (2013.01); *G01N 33/94* (2013.01); *G01N 33/9493* (2013.01); *C12Q 1/32* (2013.01)

(58) Field of Classification Search
None
See application file for complete search history.

(56) References Cited

U.S. PATENT DOCUMENTS

| | | | |
|---|---|---|---|
| 4,537,883 A | 8/1985 | Alexander et al. | |
| 4,753,965 A | 6/1988 | Stemerick et al. | |
| 4,841,085 A * | 6/1989 | Farquhar et al. | 558/180 |
| 5,036,060 A | 7/1991 | Alam et al. | |
| 5,055,459 A * | 10/1991 | Andersson et al. | 514/114 |
| 5,187,266 A * | 2/1993 | Farquhar et al. | 536/6.4 |
| 5,204,369 A | 4/1993 | Vallee et al. | |
| 5,413,995 A | 5/1995 | Alexander et al. | |
| 5,624,910 A | 4/1997 | Vallee et al. | |
| 5,649,904 A | 7/1997 | Gianni | |
| 5,866,169 A | 2/1999 | Hausheer et al. | |
| 5,876,956 A * | 3/1999 | Jones et al. | 435/26 |
| 5,886,028 A | 3/1999 | Vallee et al. | |
| 5,914,257 A * | 6/1999 | Fukaya et al. | 435/190 |
| 6,121,010 A | 9/2000 | Vallee et al. | |
| 6,255,497 B1 | 7/2001 | Vallee et al. | |
| 6,268,138 B1 * | 7/2001 | Dalla-Favera et al. | 435/6.14 |
| 6,288,110 B1 | 9/2001 | Marikovsky | |
| 6,428,782 B1 | 8/2002 | Slavin et al. | |
| 6,447,767 B1 | 9/2002 | Slavin et al. | |
| 6,465,436 B2 | 10/2002 | Lukas et al. | |
| 6,544,787 B1 * | 4/2003 | Slavin | 435/372 |
| 6,558,662 B2 | 5/2003 | Sykes et al. | |
| 6,562,347 B1 | 5/2003 | Kwak et al. | |
| 6,627,759 B1 | 9/2003 | Smith et al. | |
| 6,936,599 B2 | 8/2005 | Voskuhl | |
| 7,368,434 B2 | 5/2008 | Keung et al. | |
| 7,408,039 B2 | 8/2008 | Sykes et al. | |
| 7,531,562 B2 * | 5/2009 | Fahl et al. | 514/365 |
| 7,754,480 B2 * | 7/2010 | Smith et al. | 435/372 |
| 7,892,578 B2 * | 2/2011 | Sykes et al. | 424/577 |
| 2001/0053362 A1 | 12/2001 | Walters | |
| 2002/0048584 A1 | 4/2002 | Pomerantz | |
| 2003/0007968 A1 | 1/2003 | Larsen et al. | |
| 2003/0073649 A1 | 4/2003 | DiMartino et al. | |
| 2003/0099622 A1 | 5/2003 | Hering et al. | |
| 2004/0023318 A1 * | 2/2004 | Smith et al. | 435/25 |
| 2004/0064037 A1 | 4/2004 | Smith | |
| 2004/0152630 A1 | 8/2004 | Fu et al. | |
| 2004/0214902 A1 | 10/2004 | Wang et al. | |
| 2005/0108067 A1 | 5/2005 | Chapman et al. | |
| 2005/0201980 A1 | 9/2005 | Moran | |
| 2005/0272698 A1 | 12/2005 | Daftary et al. | |

(Continued)

FOREIGN PATENT DOCUMENTS

WO    WO-96/36344       11/1996
WO    WO-98/20932 A2    5/1998

(Continued)

OTHER PUBLICATIONS

Adamkiewicz, T.V. et al. "Unrelated cord blood transplantation in children with sickle cell disease: Review of four-center experience" *Pediatr Transplantation*, 2007, 11:641-644.

(Continued)

*Primary Examiner* — Renee Claytor
*Assistant Examiner* — Susan E Fernandez
(74) *Attorney, Agent, or Firm* — Foley Hoag LLP

(57) ABSTRACT

The present invention provides methods of identifying subjects that are suitable and not suitable for high-dose cyclophosphamide treatment.

10 Claims, No Drawings

(56) References Cited

U.S. PATENT DOCUMENTS

| | | |
|---|---|---|
| 2006/0002930 A1 | 1/2006 | Brunetta et al. |
| 2006/0229233 A1 | 10/2006 | Frenkel et al. |
| 2006/0253263 A1 | 11/2006 | Meshkin |
| 2007/0173442 A1 | 7/2007 | Vollmer |
| 2007/0202077 A1 | 8/2007 | Brodsky et al. |
| 2011/0082115 A1 | 4/2011 | O'Donnell, Jr. et al. |
| 2011/0092462 A1 | 4/2011 | Brodsky et al. |
| 2011/0097426 A1 | 4/2011 | O'Donnell, Jr. et al. |
| 2011/0117050 A1 | 5/2011 | O'Donnell, Jr. et al. |

FOREIGN PATENT DOCUMENTS

| | | |
|---|---|---|
| WO | WO-98/42378 | 10/1998 |
| WO | WO-99/42099 | 8/1999 |
| WO | WO-00/27428 | 5/2000 |
| WO | WO-00/40701 A2 | 7/2000 |
| WO | WO-00/74718 | 12/2000 |
| WO | WO-2005/057213 A1 | 6/2005 |
| WO | WO-2007/065167 | 6/2007 |
| WO | WO-2008/034071 | 3/2008 |
| WO | WO-2008/034074 | 3/2008 |
| WO | WO-2008/034076 | 3/2008 |
| WO | WO-2008/156494 | 12/2008 |
| WO | WO-2009/045464 | 4/2009 |
| WO | WO-2009/067690 A2 | 5/2009 |
| WO | WO-2009/067699 A2 | 5/2009 |
| WO | WO-2009/094456 | 7/2009 |

OTHER PUBLICATIONS

Alyea, E.P. et al. "Comparative outcome of nonmyeloablative and myeloablative allogeneic hematopoietic cell transplantation for patients older than 50 years of age" Blood, Feb. 15, 2005, 105(4):1810-1814.

Alyea, E.P. et al. "Impact of Conditioning Regimen Intensity on Outcome of Allogeneic Hematopoietic Cell Transplantation for Advanced Acute Myelogenous Leukemia and Myelodysplastic Syndrome" Biology of Blood and Marrow Transplantation, 2006, 12:1047-1055.

Attema-De Jonge, M.E. "Pharmacokinetically guided dosing of (high-dose) chemotherapeutic agents" Thesis University Utrecht, Dec. 17, 2004, pp. 1-313.

Bacigalupo, A. et al. "Defining the Intensity of Conditioning Regimens: working definitions" Biol Blood Marrow Transplant, Dec. 2009, 15(12):1628-1633.

Baron, F. et al. "Allogeneic Hematopoietic Cell Transplantation Following Nonmyeloablative Conditioning as Treatment for Hematologic Malignancies and Inherited Blood Disorders" Molecular Therapy, Jan. 2006, 13(1):26-41.

Bernaudin, F. et al. "Long-term results of related myeloablative stem-cell transplantation to cure sickle cell disease" Blood, Oct. 1, 2007, 110(7):2749-2756.

Brodsky, R.A. et al. "Multicenter phase 3 study of the complement inhibitor eculizumab for the treatment of patients with paroxysmal nocturnal hemoglobinuria" Blood, Feb. 15, 2008, 111(4):1840-1847.

Brodsky, R.A. "Reduced intensity HLA-haploidentical BMT with post transplantation cyclophosphamide in nonmalignant hematologic diseases" Bone Marrow Transplant, Oct. 2008, 42(8):523-527.

Brown, R.A. et al. "High-Dose Etoposide, Cyclophosphamide, and Total Body Irradiation With Allogeneic Bone Marrow Transplantation for Patients With Acute Myeloid Leukemia in Untreated First Relapse: A Study by the North American Marrow Transplant Group" Blood, Mar. 1, 1995, 85(5):1391-1395.

Burroughs, L. et al. "Comparison of Allogeneic Hematopoietic Cell Transplantation (HCT) after Nonmyeloablative Conditioning with HLA-Matched Related (MRD), Unrelated (URD), and Related Haploidentical (Haplo) Donors for Relapsed or Refractory Hodgkin Lymphoma (HL)" Blood (ASH Annual Meeting Abstracts), 2007, 110: Abstract 173.

Burroughs, L.M. et al. "Comparison of Outcomes of HLA-Matched Related, Unrelated, or HLA-Haploidentical Related Hematopoietic Cell Transplantation following Nonmyeloablative Conditioning for Relapsed or Refractory Hodgkin Lymphoma" Biol Blood Marrow Transplant, Nov. 2008, 14(11):1279-1287.

Demirer, T. et al. "High-Dose Cyclophosphamide, Carmustine, and Etoposide Followed by Allogeneic Bone Marrow Transplantation in Patients With Lymphoid Malignancies Who Had Received Prior Dose-Limiting Radiation Therapy" J Clin Oncol, Mar. 1995, 13(3):596-602.

Dezern, A.E. et al. "Post-transplantation cyclophosphamide for GVHD prophylaxis in severe aplastic anemia" Bone Marrow Transplantation, 2010, pp. 1-2.

Djulbegovic, B. et al. "Nonmyeloablative Allogeneic Stem-Cell Transplantation for Hematologic Malignancies: A Systematic Review" Cancer Control, 2003, 10(1):17-41.

Droz, J.P. et al. "Failure of High-Dose Cyclophosphamide and Etoposide Combined with Double-Dose Cisplatin and Bone Marrow Support in Patients with High-Volume Metastatic Nonseminomatous Germ-Cell Tumours: Mature Results of a Randomised Trial" European Urology, 2007, 51:739-748.

Eto, M. et al. "Specific Destruction of Host-Reactive Mature T Cells of Donor Origin Prevents Graft-Versus-Host Disease in Cyclophosphamide-Induced Tolerant Mice" The Journal of Immunology, Mar. 1, 1991, 146(5):1402-1409.

Hess, D.A. et al. "Selection based on CD133 and high aldehyde dehydrogenase activity isolates long-term reconstituting human hematopoietic stem cells" Blood, Mar. 1, 2006, 107(5):2162-2169.

Hillmen, P. et al. "The Complement Inhibitor Eculizumab in Paroxysmal Nocturnal Hemoglobinuria" N Engl J Med, Sep. 21, 2006, 355(12):1233-1243.

Horan, J.T. et al. "Hematopoietic stem cell transplantation for multiply transfused patients with sickle cell disease and thalassemia after low-dose total body irradiation, fludarabine, and rabbit anti-thymocyte globulin" Bone Marrow Transplantation, 2005, 35:171-177.

Hsu, Frank J., et al. "Vaccination of patients with B-cell lymphoma using autologous antigen-pulsed dendritic cells," Nature Medicine, 2(1):52-58 (Jan. 1996).

Huzly, D. et al. "Routine Immunizations in Adult Renal Transplant Recipients." Transplantation, 63:839-845. Published Mar. 1997.

Iannone, R. et al. "Results of Minimally Toxic Nonmyeloablative Transplantation in Patients with Sickle Cell Anemia and β-Thalassemia" Biology of Blood and Marrow Transplantation, 2003, 9:519-528.

Jalla, S. et al. "Cyclophosphamide Plus Allogeneic CD4+ T Cell Infusion Induces Anti-Lymphoma Immunity Despite Lack of Graft-Versus-Host Disease (GVHD) or Sustained Engraftment" Blood (ASH Annual Meeting abstracts), 2004, 104: Abstract 3063.

Kasamon, Y.L. et al. "Greater HLA Disparity Is Associated with Reduced Risk of Relapse and Improved Event-Free Survival after Nonmyeloablative, HLA-Haploidentical BMT with Post-Transplantation High-Dose Cyclophosphamide" Blood (ASH Annual Meeting abstracts), 2008, 112: Abstract 150.

Kasamon, Y.L. et al. "Immunologic recovery following autologous stem-cell transplantation with pre- and posttransplantation rituximab for low-grade or mantle cell lymphoma" Annels of Oncology, Jun. 2010, 21(6):1203-1210.

Kasamon, Y.L. et al. "Nonmyeloablative HLA-Haploidentical BMT with High-Dose Posttransplantation Cyclophosphamide: Effect of HLA Disparity on Outcome" Biol Blood Marrow Transplant, Apr. 2010, 16(4):482-489.

Levy, M.Y. et al. "Clinical Tumor Responses Despite Graft Rejection after Nonmyeloablative Conditioning and Transplantation of Partially HLA-Mismatched (Haploidentical) Bone Marrow" Blood (ASH Annual Meeting Abstracts), 2005, 106: Abstract 2897.

Ljungman, P. et al. "Special Report: Vaccination of stem cell transplant recipients: recommendations of the Infectious Diseases Working Party of the EBMT" Bone Marrow Transplantation, 2005, 35:737-746.

Luznik, L. et al. "High-dose cyclophosphamide as single-agent, short-course prophylaxis of graft-versus-host disease" Blood, Apr. 22, 2010, 115(16):3224-3230.

(56) References Cited

OTHER PUBLICATIONS

Luznik, L. et al. "High-dose cyclophosphamide for graft-versus-host disease prevention" *Current Opinion in Hematology*, 2010, 17:493-499.
Luznik, L. et al. "High-dose, post-transplantation cyclophosphamide to promote graft-host tolerance after allogeneic hematopoietic stem cell transplantation" *Immunol Res*, 2010, 47:65-77.
Luznik, L. et al. "HLA-Haploidentical Bone Marrow Transplantation for Hematologic Malignancies Using Nonmyeloablative Conditioning and High-Dose, Posttransplantation Cyclophosphamide" *Biol Blood Marrow Transplant*, Jun. 2008, 14(6):641-650.
Luznik, L. et al. "Nonmyeloablative alternative donor transplants" *Current Opinion in Oncology*, 2003, 15:121-126.
Luznik, L. et al. "Posttransplantation Cyclophosphamide Facilitates Engraftment of Major Histocompatibility Complex-Identical Allogeneic Marrow in Mice Conditioned With Low-Dose Total Body Irradiation" *Biology of Blood and Marrow Transplantation*, 2002, 8:131-138.
Luznik, L. et al. "Post-transplantation high dose cyclophosphamide (CY) is effective single agent for prevention of acute and chronic graft versus host disease after myeloablative HLA matched related and unrelated bone marrow transplantation (BMT)" *Blood (ASH Annual Meeting Abstracts)*, 2008, 112: Abstract 56.
Mayumi, H. et al. "Cyclophosphamide-Induced Immunological Tolerance: an Overview" *Immunobiol.*, 1996, 195:129-139.
Mayumi, H. et al. "Drug-Induced Tolerance to Allografts in Mice" *Transplantation*, 1987, 44(2):286-290.
Mentzer, W.C. et al. "Availability of Related Donors for Bone Marrow Transplantation in Sickle Cell Anemia" *Am. J. Pediatr. Hematol. Onco.*, 1994, 16(1):27-29.
Mielcarek, M. et al. "Graft-versus-host disease after nonmyeloablative versus conventional hematopoietic stem cell transplantation" *Blood*, Jul. 15, 2003, 102(2):756-762.
Mink, S.A. et al. "High-Dose Therapy in Lymphomas: A Review of the Current Status of Allogeneic and Autologous Stem Cell Transplantation in Hodgkin's Disease and Non-Hodgkin's Lymphoma" *The Oncologist*, 2001, 6:247-256.
Moyo, Victor M., et al. "High-dose cyclophosphamide for refractrory autoimmune hemolytic anemia," Blood, 100(2) :704-706 (Jul. 15, 2002), XP-002430101.
Noonan, K. et al. "Enrichment of Allogeneic Tumor Antigen-Specific T Cells From Bone Marrow (BM) of Patients Treated with High-Dose Post-Transplant Cyclophoshamide (Cy)—A Novel Approach to Adoptive Immunotherapy" *Blood (ASH Annual Meeting Abstracts)*, 2011, 118: Abstract 647.
O'Donnell, P. et al. "Favorable Outcome of Patients with Relapsed Hodgkin Lymphoma (HL) after Nonmyeloablative Cell Transplantation (NM-HCT) Using Related Haploidentical Donors" *Blood (ASH Annual Meeting Abstracts)*, 2006, 108: Abstract 3135.
O'Donnell, P.V. et al. "Nonmyeloablative Bone Marrow Transplantation from Partially HLA-Mismatched Related Donors Using Posttransplantation Cyclophosphamide" *Biology of Blood and Marrow Transplantation*, 2002, 8:377-386.
Openshaw, H. et al. "Peripheral Blood Stem Cell Transplantation in Multiple Sclerosis With Busulfan and Cyclophosphamide Conditioning: Report of Toxicity and Immunological Monitoring" *Biology of Blood and Marrow Transplantation*, 2000, 6:563-575.
Panepinto, J.A. et al. "Matched-related donor transplantation for sickle cell disease: report from the Center for International Blood and Transplant Research" *British Journal of Haematology*, 2007, 137:479-485.
Perry, J.J. et al. "Administration and pharmacokinetics of high-dose cyclophosphamide with hemodialysis support for allogeneic bone marrow transplantation in acute leukemia and end-stage renal disease" *Bone Marrow Transplantation*, 1999, 23:839-842.
Peters, W.P. et al. "High-Dose Combination Alkylating Agents With Bone Marrow Support as Initial Treatment for Metastatic Breast Cancer" *J Clin Oncol*, Sep. 1988, 6(9):1368-1376.
Petrus, M.J. et al. "An Immunoablative Regimen of Fludarabine and Cyclophosphamide Prevents Fully MHC-Mismatched Murine Marrow Graft Rejection Independent of GVHD" *American Society for Blood and Marrow Transplantation*, 2000, pp. 182-189.
Rossi, H.A. et al. "High-dose cyclophosphamide, BCNU, and VP-16 (CBV) conditioning before allogeneic stem cell transplantation for patients with non-Hodgkin's lymphoma" *Bone Marrow Transplantation*, 2003, 31:441-446.
Rother, R.P. et al. "Discovery and development of the complement inhibitor eculizumab for the treatment of paroxysmal nocturnal hemoglobinuria" *Nature Biotechnology*, Nov. 2007, 25(11):1256-1264.
Ruggieri, M. et al. "Glatiramer Acetate in Multiple Sclerosis: A Review" *CNS Drug Reviews*, 2007, 13(2):178-191.
Snowden, J.A. "Haemopoetic Stem Cell Transplantation in Autoimmune Disease" Bangkok, Thailand, Oct. 24-28, 1999, pp. 180-183.
Spitzer, T.R. "Nonmyeloablative Allogeneic Stem Cell Transplant Strategies and the Role of Mixed Chimerism" *The Oncologist*, 2000, 5:215-223.
Storb, R. et al. "Marrow Transplantation From HLA-Identical Siblings for Treatment of Aplastic Anemia: Is Exposure to Marrow Donor Blood Products 24 Hours Before High-Dose Cyclophosphamide Needed for Successful Engraftment?" *Blood*, Apr. 1983, 61(4):672-675.
Symons, H. et al. "HLA-Haploidentical Bone Marrow Transplantation (BMT) for High Risk Hematologic Malignancies Using Myeloablative Conditioning and High-Dose, Posttransplantation Cyclophosphamide" *Blood (ASH Annual Meeting Abstracts)*, 2010, 116: Abstract 2362.
Symons, H.J. et al. "Impact of Killer Immunoglobulin Receptor (KIR) Ligand Incompatibility in Nonmyeloablative Bone Marrow Transplantation (BMT) from Haploidentical Donors" *Blood (ASH Annual Meeting Abstracts)*, 2006, 108: Abstract 604.
Symons, H.J. et al. "Improved survival with inhibitory Killer Immunoglobulin Receptor (KIR) gene mismatches and KIR haplotype B donors after nonmyeloablative, HLA-haploidentical bone marrow transplantation" *Biol Blood Marrow Transplant*, Apr. 2010, 16(4):533-542.
Symons, H.J. et al. "Low Incidence of CMV Reactivation and Infectious Morbidity and Mortality after Nonmyeloablative Haploidentical Bone Marrow Transplantation Incorporating Post-Transplantation Cyclophosphamide" *Blood (ASH Annual Meeting Abstracts)*, 2005, 106: Abstract 3245.
Symons, H.J. et al. "Low Incidence of CMV Reactivation and Infection after Allogeneic Bone Marrow Transplantation (BMT) Incorporating Post-Transplantation Cyclophosphamide (Cy)" *Blood (ASH Annual Meeting Abstracts)*, 2006, 108: Abstract 2859.
Takahashi, Y. et al. "In vitro and in vivo evidence of PNH cell sensitivity to immune attack after nonmyeloablative allogeneic hematopoietic cell transplantation" *Blood*, Feb. 15, 2004, 103(4):1383-1390.
Toze, C.L. et al. "Myeloablative allografting for chronic lymphocytic leukemia: evidence for a potent graft-versus-leukemia effect associated with graft-versus-host disease" *Bone Marrow Transplantation*, 2005, 36:825-830.
Van Besien, K. et al. "Fludarabine-based conditioning for allogeneic transplantation in adults with sickle cell disease" *Bone Marrow Transplantation*, 2000, 26:445-449.
Vose, J.M. "Single Dose Pegfilgrastin (SD/01) Is as Effective as Daily Filgrastim Following ESHAP Chemotherapy for Subjects with Non-Hodgkin's Lymphoma or Hodgkin's Disease: Results of a Randomized, Open-Label Study" OncoLink Scientific Meetings Coverage, held Tuesday, Dec. 11, 2001, retrieved from http://www.oncolink.org/conferences/article.cfm?id=490.
Walters, M.C. "Cord blood transplantation for sickle cell anemia: Bust or boom?" *Pediatr Transplantation*, 2007, 11:582-583.
Zhou, X. et al. "Synergy between Nonmyeloablative Doses of Intravenous Busulfan and Post-Transplantation Cyclophosphamide for Induction of Tolerance to MHC-Compatible Stem Cell Allografts" *Blood, (ASH Annual Meeting Abstracts)*, 2005, 106: Abstract 3040.
Davis et al., "Idiotype Vaccination Following ABMT Can Stimulate Specific Anti-Idiotype Immune Responses in Patients With B-Cell Lymphoma," Biology of Blood and Marrow Transplantation, 7:517-522 (2001).

(56) References Cited

OTHER PUBLICATIONS

Leandro et al., "An Open Study of B Lymphocyte Depletion in Systemic Lupus Erythematosus," Arthritis & Rheumatism, 46(10):2673-2677 (2002).
Pallera et al., "Managing the Toxicity of Hematopoietic Stem Cell Transplant," J. Support. Oncol., 2(3):223-247 (2004).
International Search Report dated Jun. 7, 2007, from PCT/US2006/061549.
International Search Report dated Nov. 6, 2008, from PCT/US2007/078518.
International Search Report dated Jan. 29, 2009, from PCT/US2007/078521.
International Search Report dated Jan. 8, 2009, from PCT/US2007/078524.
International Search Report dated Dec. 24, 2008, from PCT/US07/81614.
Supplementary European Search Report dated Apr. 27, 2011 from EP 11 00 1548.
Chung, D. et al., "Anti-Thymocyte Globulin Prevents Autoimmune Encephalomyelitis by Expanding Myelin Antigen Specific Foxp3+ Regulatory T Cell," Clinical Immunology, 123:S10-S11 (2007) Abstract.
Maksymowych et al., "Evaluation and Validation of the Patient Acceptable Symptom State (PASS) in Patients With Ankylosing Spondylitis," Arthritis & Rheumatism, 57(1):133-139 (2007).
Mickey, M.R. et al., "Correlation of Clinical and Immunologic States in Multiple Sclerosis," Arch Neurol, 44:371-375 (1987).
Moody, D.J. et al., "Administration of Monthly-Pulse Cyclophosphamide in Multiple Sclerosis Patients. Effects of Long-Term Treatment on Innunologic Parameters," J. Neuroimmunology, 14:161-173 (1987).
Moreb et al., "Heterogeneity of Aldehyde Dehydrogenase Expression in Lung Cancer Cell Lines is Revealed by Aldefluor Flow Cytometry-Based Assay," Cytometry Part B (Clin Cyto), 72B:281-289 (2007).
Uitdehaag, B.M.J. et al., "Long-Lasting Effects of Cyclophosphamide on Lymphocytes in Peripheral Blood and Spinal Fluid," Acta Neurol. Scand., 79:12-17 (1989).
European Search Report dated Oct. 17, 2011 from EP 08836174.6.
International Search Report dated Dec. 16, 2008, from PCT/US08/11402.
Awad, A. et al., "Cyclophosphamide in Multiple Sclerosis: Scientific Rationale, History and Novel Treatment Paradigms," Ther Adv Neurol Disord, 2(6):357-368 (2009).
Brannagan, T.H., 3rd, Alaedini, A., Gladstone, D.E. "High-dose cyclophosphamide without stem cell rescue for refractory multifocal motor neuropathy," Muscle Nerve, Aug.;34(2):246-50 (2006).
Brannagan, T.H. et al., "High-dose Cyclophosphamide Without Stem-cell Rescue for Refractory CIDP," Neurology, 58:1856-1858 (2002).
Brodsky, R.A., "Acquired Severe Aplastic Anemia in Children: Is there a standard of care?" Pediatric Blood and Cancer, 43(7):711-2 (2004).
Brodsky, R.A., Smith, B.D., "Bone marrow transplantation for autoimmune diseases," Current Opinion in Oncology, 11: 83-86 (1999).
Brodsky, R.A., "Biology and management of acquired severe aplastic anemia," Current Opinion in Oncology, 10:95-99 (1998) (abstract only).
Brodsky, Robert, A., et al.; "Complete Remission in Severe Aplastic Anemia After High-Dose Cyclophosphamide Without Bone Marrow Transplantation", Blood, vol. 87, No. 2, Jan. 15, 1996, pp. 491-494.
Brodsky, Robert A., et al.; "Durable Treatment-Free Remission after High-Dose Cyclophosphamide Therapy for Previously Untreated Severe Aplastic Anemia", vol. 135 No. 7, Oct. 2, 2001, pp. 477-483.
Brodsky, Robert A., et al.; "Elimination of alloantibodies by immunoablative high-dose cyclophosphamide" Transplantation (Baltimore), vol. 71, No. 3, Feb. 15, 2001; pp. 482-484, XP009082021 (ISSN: 0041-1337).
Brodsky, Robert A., et al.; "High-dose cyclophosphamide as salvage therapy for severe aplastic anemia," Experimental Hematology (New York), vol. 32, No. 5, May 2004; pp. 435-440, XP002430102 (ISSN: 0301-472X).
Brodsky, R.A., "High dose cyclophosphamide treatment for autoimmune disorders," The Scientific World Journal 2:1808-1815 (2002).
Brodsky, R.A., "High-dose cyclophosphamide for aplastic anemia and autoimmunity," Current Opinion in Oncology, 14:143-146 (2002).
Brodsky, Robert, A., et al.; "Immunoablative High-Dose Cyclophosphamide without stem-Cell Rescue for Refractory, Severe Autoimmune Disease", vol. 129, Issue 12, Dec. 15, 1998, pp. 1031-1035.
Brodsky, R.A., Jones, R.J., "Riddle: What do aplastic anemia, acute promyelocytic leukemia, and chronic myeloid leukemia have in common?" Leukemia, 18(10):1740-2 (2004).
DeAngelis, T. et al., "Multiple Sclerosis: New Treatment Trials and Emerging Therapeutic Targets," Neurology, 21:261-271 (2008).
D'Cruz, D. et al., "High-dose Intravenous Cyclophosphamide Therapy in Severe SLE," Lupus, 11:403-404 (2002).
de Bittencourt, P.R.M. et al., "Multiple sclerosis: long-term remission after a high dose of cyclophosphamide," Acta Neurol Scan, 111:195-198 (2005).
Drachman, Daniel B., et al.; "High-dose therapy for autoimmune neurologic diseases," Current Opinion in Oncology; vol. No. 2, Mar. 2005; pp. 83-88, XP009082245 (ISSN: 1040-8746).
Drachman, Daniel B., et al.; "Treatment of refractory myasthenia: "Rebooting" with high-dose cyclophosphamide," Annals of Neurology, vol. 53, No. 1, Jan. 2003, pp. 29-34, XP009082013 (ISSN: 0364-5134 Abstract).
Freeman E., "High Time for HiCy," Hopkins Medicine, pp. 21-26, Winter 2008.
Fuchs et al., "Post-transplantation cyclophosphamide (CY) reduces graft rejection and graftversus-host disease (GVHD) after non-myeloblative, partially HLA-mismatched (haploidentical) bone marrow transplantation (BMT)," Blood, 104(11):128A, Abstract.
Gauthier, S.A. et al., "Cyclophosphamide Therapy for MS," The International MS Journal, 12:52-58 (2005).
Gladstone, DE, et al., "High-dose Cyclophosphamide for Severe Systemic Lupus Erythematous," Lupus, 11:405-410 (2002).
Gladstone, D.E. et al., "High-Dose Cyclophosphamide for Moderate to Severe Refractory Multiple Sclerosis," Arch Neurol, 63:1388-1393 (2006).
Gladstone, D.E. and Brannagan, T.H., "High dose cyclophosphamide for severe refractory myasthenia gravis," Journal of Neurology, Neurosurgery and Psychiatry, 75:789-791 (2004).
Gladstone, D.E., Prestrud, A.A., Brannagan, T.H., 3rd., "High-dose cyclophosphamide results in long-term disease remission with restoration of a normal quality of life in patients with severe refractory chronic inflammatory demyelinating polyneuropathy," J Peripher Nery Syst., Mar. ;10(1):11-6 (2005).
Huhn, Richard D., et al.; High-dose Cyclophosphamide with Autologous Lymphocyte-depleted Peripheral Blood Stem Cell (PFCS) Support for Treatment of Refractory Chronic Autoimmune Thrombocytopenia, Blood, vol. 101, No. 1, Jan. 1, 2003, pp. 71-77.
Kerr D. et al., "Revimmune: Delivering a knockout punch to autoimmune diseases," Specialty Pharma—Therapeutic Focus, 7, vol. 7, No. 6, pp. 80-83 (Jun. 2007).
Krishnan, Drachman, et al. "High-Dose Cyclophosphamide in the Treatment of Aggressive Multiple Sclerosis," (American Academy of Neurology (AAN) Annual Meeting: 2006 Abstract (Apr. 4, 2006).
Krishnan, C. et al., "Reduction of Disease Activity and Disability With High-Dose Cyclophosphamide in Patients With Aggressive Multiple Sclerosis," Arch Neurol, 65(8):E1-E8 (2008).
Krishnan, C. et al., "Reduction of Disease Activity and Disability with High-Dose Cyclophosphamide in Patients With Aggressive Multiple Sclerosis," Arch Neurol., 65(8):1044-1051 (2008).
La Mantia, L. et al., "Cyclophosphamide for multiple sclerosis (Review)," Cochrane Database of Systematic Reviews 2002, 3:1-22.
La Mantia, L. et al., "Cyclophosphamide for multiple sclerosis (Review)," Cochrane Database of Systematic Reviews 2007, 1:1-23.

(56) References Cited

OTHER PUBLICATIONS

Lin, P.T., Martin, B.A., Weinacker, A.B., So, Y.T., "High-dose cyclophosphamide in refractory myasthenia gravis with MuSK antibodies," Muscle Nerve, Mar. ; 33:433-5 (2006).

Luznik et al., "Durable engraftment of major histocompatibility complex-incompatible cells after nonmyeloablative conditioning with fludarabine, low-dose total body irradiation, and posttransplantation cyclophosphamide," Blood, 98:3456-3464 (2001).

Luznik, et al., "Post-Transplantation High-Dose Cyclophosphamide (CY) Is Effective Single Agent GVHD Prophylaxis That Permits Prompt Immune Reconstitution after Myeloablative HLA Matched Related and Unrelated Bone Marrow Transplantation (BMT)," Session Type: Poster Session, Board #120-III, presented at American Society of Hematology (ASH) Annual Meeting Dec. 11, 2006; Abstract #2891 appears in Blood, vol. 108, issue 11, (Nov. 16, 2006).

Luznik, et al., "Post-Transplantation high-dose cyclophosphamide (CY) is an effective single agent GVHD prophylaxis that permits prompt immune reconstitution after myeloablative HLA matched related and unrelated bone marrow transplantation (BMT)," Biology of Blood and Marrow Transplantation, vol. 13, Issue 2, Supplement 1, (Feb. 2007), p. 4, Abstracts from the 2007 BMT Tandem Meetings; Available online Jan. 25, 2007.

McGuire, T.R. et al., "High-dose Cyclophosphamide in multiple sclerosis patients undergoing autologous stem cell transplantation," International Immunopharmacology, 3:279-283 (2003).

Moyo, V.M., Smith, B.D., Brodsky, I., Crilley, P., Jones, R.J., Brodsky, R.A. "High-dose cyclophosphamide for refractrory autoimmune hemolytic anemia," Blood, 100:704-706 (2002), XP-002430101.

Nousari, Carlos, H., et al.; "Evaluating the role of immunoablative high-dose cyclophosphamide therapy in pemphigus vulgaris," Journal of the American Academy of Dermatology; vol. 49, No. 1, Jul. 2003; pp. 148-150, XP002430103 (ISSN: 0190-9622).

Nousari, H.C., Brodsky, R.A., Jones, R.J., Greyer, M.R., Anhalt, G.J., "Immunoablative high-dose cyclophosphamide without stem cell rescue in paraneoplastic pemphigus: Report of a case and review of this new therapy for severe autoimmune disease," Journal of the American Academy of Dermatology, 40:750-754 (1999).

Perini, P. et al., "Cyclophosphamide is effective in stabilizing rapidly deteriorating secondary progressive multiple sclerosis," J Neurol 250:834-838 (2003).

Petri, Michelle, et al.; "High-dose cyclophosphamide without stem cell transplantation in systemic lupus erythematosus," Arthritis and Rheumatism Jan. 2003; vol. 48, No. 1, Jan. 2003 pp. 166-173; XP009082020 (ISSN: 0004-3591 Abstract).

Prestrud, A.A. et al., "High-dose Cyclophosphamide Therapy Without Stem Cell Rescue for Severe Refractory Autoimmune Illnesses: Comment on the Article by Moore et al." Arthritis & Rheumatism, 48(5):1461-1470 (2003).

Santos, G. W. et al.; "The Use of Cyclophosphamide for Clinical Marrow Transplantation," Transplantation Proceedings, vol. 4, No. 4, 1972, pp. 559-564, XP009082012 (ISSN: 0041-1345).

Savage, W.J. et al. "Treatment of Hepatitis-Associated Aplastic Anemia with High Dose Cyclophosphamide," ASH 2006, Session Type: Poster Session, Board #103-I; Abstract 179, (Dec. 9, 2006); Abstract 975 appears in Blood, vol. 108, issue 11, (Nov. 16, 2006).

Schwartzman, R.J. et al., "High-Dose Cyclophosphamide in the Treatment of Multiple Sclerosis," Neuroscience & Therapeutics 15:118-127 (2009).

Sehgal et al., "Infectious Complications of High-Dose Cyclophosphamide Treatment in Autoimmune Disease," Blood (ASH Annual Meeting Abstracts), 104:Abstract 5091 (2004).

Shammo, J. et al., "Immune Ablation Using High-Dose Cyclophosphamide without Stem Cell Rescue for Intractable Multiple Sclerosis," Blood (ASH Annual Meeting Abstracts) 106: Abstract 5504 (2005).

Smith, D. R., et al.: "A randomized blinded trial of combination therapy with cyclophosphamide in patients with active multiple sclerosis on interferon beta" Multiple Sclerosis, vol. 11, No. 5, Oct. 2005, pp. 573-582, XP009082240 (ISSN: 1352-4585).

Swinnen L.J. et al., "Phase II Study of High Dose Outpatient Cyclophosphamide and Rituximab, without Stem Cell Support, for Low Grade and Mantle Cell Lymphoma," ASH 2006, Session Type: Poster Session, Board #919-II; Abstract 2741, (Dec. 10, 2006); Abstract 2741 appears in Blood, vol. 108, issue 11, (Nov. 16, 2006).

Weiner, H. L., et al.; "Treatment of multiple sclerosis with cyclophosphamide: Critical review of clinical and immunologic effects," Multiple Sclerosis, vol. 8, No. 2, Apr. 2002, pp. 142154, XP009082459 (ISSN: 1352-4585).

Today's Sunbeam Article, "For Pennsville woman with MS, new treatment has been 'just a miracle," post Apr. 25, 2004.

USA Today Article, "Researchers say large doses of chemo drug may fight MS," Posted Mar. 23, 2004.

Anderson, L.W. et al. "Cyclophosphamide and 4-Hydroxycyclophosphamide/Aldophosphamide Kinetics in Patients Receiving High-Dose Cyclophosphamide Chemotherapy" *Clinical Cancer Research*, Sep. 1996, 2:1481-1487.

"Biovest Secures Worldwide Exclusive License to Late-Stage Technology for Elimination of Transplant Rejection" Press Release, Jan. 22, 2008 at 08:30 AM EST.

Brien, J.F. et al. "Aldehyde dehydrogenase inhibitors as alcohol-sensitizing drugs: a pharmacological perspective" *TIPS*, Dec. 1985, 477-480.

Cohen, L. "Optimization of Dose-Time Factors for a Tumor and Multiple Associated Normal Tissues" Int. J. Radiation Oncology Biol. Phys., Feb. 1987, 13(2):251-258.

Dockham, P.A. et al. "Relative Contribution of Human Erythrocyte Aldehyde Dehydrogenase to the Systemic Detoxification of the Oxazaphosphorines" Drug Metabolism and Disposition, 1997, 25(12):1436-1441.

Emadi, A. et al. "Cyclophosphamide and cancer: golden anniversary" Nat. Rev. Clin. Oncol., Nov. 2009, 6:638-647.

Germolec, D.R. et al. "Induction of CYP1A1 and ALDH-3 in Lymphoid Tissues from Fisher 344 Rats Exposed to 2,3,7,8-Tetrachlorodibenzodioxin (TCDD)" Toxicology and Applied Pharmacology, 1996, 137:57-66.

Ginestier, C. et al. "ALDH1 is a marker of normal and malignant human mammary stem cells and a predictor of poor clinical outcome" Cell Stem Cell, Nov. 15, 2007, 1(5):555-567.

Groot et al. "Aldehyde Dehydrogenase Involvement in a variant of the Brown Norway Rat Acute Myelocytic Leukemia (BNML) that acquired cyclophosphamide resistance in vivo" European Journal of Cancer, vol. 30A, No. 14, pp. 2137-2143, 1994.

Hacker, M.P. et al. "Effect of Disulfiram (Tetraethylthiuram Disulfide) and Diethyldithiocarbamate on the Bladder Toxicity and Antitumor Activity of Cyclophosphamide in Mice" Cancer Research, Nov. 1982, 42:4490-4494.

Hadidi, A.H.F.A. et al. "Phenotypically Deficient Urinary Elimination of Carboxyphosphamide after Cyclophosphamide Administration to Cancer Patients" Cancer Research, Sep. 15, 1988, 48:5167-5171.

Hansell, N. K. et al. "Erythrocyte Aldehyde Dehydrogenase Activity: Lack of Association with Alcohol Use and Dependence or Alcohol Reactions in Australian Twins" Alcohol & Alcoholism, 2005, 40(5):343-348.

Helander, A. et al. "Comparison of Blood Aldehyde Dehydrogenase Activities in Moist Snuff Users, Cigarette Smokers and Nontobacco Users" Alcohol Clin Exp Res, 1991, 15(1):1-6.

Helander, A. "Aldehyde Dehydrogenase in Blood: Distribution, Characteristics and Possible Use as Marker of Alcohol Misuse" Alcohol & Alcoholism, 1993, 28(2):135-145.

Henze, T. "Managing Specific Symptoms in People with Multiple Sclerosis" The International MS Journal, 2005, 12:60-68.

Hilton, J. "Role of Aldehyde Dehydrogenase in Cyclophosphamide-resistant L1210 Leukemia" Cancer Res, Nov. 1, 1984, 44:5156-5160.

Jeavons, C.M. et al. "Effects of Elevated Female Sex Steroids on Ethanol and Acetaldehyde Metabolism in Humane" Alcohol Clin Exp Res, 1984, 8(4):352-358.

Jones, R.J. et al. "Assessment of Aldehyde Dehydrogenase in Viable Cells" Blood, May 15, 1995, 85(10):2742-2746.

Kastan, M.B. et al. "Direct Demonstration of Elevated Aldehyde Dehydrogenase in Human Hematopoietic Progenitor Cells" Blood, May 15, 1990, 75(10):1947-1950.

(56) References Cited

OTHER PUBLICATIONS

Kohn, F.R. et al. "Aldehyde Dehydrogenase Activity as the Basis for the Relative Insensitivity of Murine Pluripotent Hematopoietic Stem Cells to Oxazaphosphorines" Biochemical Pharmacology, 1985, 34(19):3465-3471.

Kohn, F.R. et al. "Effect of Aldehyde Dehydrogenase Inhibitors on the ex Vivo Sensitivity of Human Multipotent and Committed Hematopoietic Progenitor Cells and Malignant Blood Cells to Oxazaphosphorines" Cancer Research, Jun. 15, 1987, 47:3180-3185.

Kohn, F.R. et al. "Effect of Aldehyde Dehydrogenase Inhibitors on the ex Vivo Sensitivity of Murine Late Spleen Colony-Forming Cells (Day-12 CFU-S) and Hematopoietic Repopulating Cells to Mafosfamide (Asta Z 7557)" Biochemical Pharmacology, 1987, 36(17):2805-2811.

Kumar, P. et al. "Chemoprotective action of Septilin against Cyclophosphamide Toxicity" Indian Journal of Pharmaceutical Sciences, 1995, 57(5):215-217.

Kwak, L.W. et al. "Vaccination with syngeneic, lymphoma-derived immunoglobulin idiotype combined with granulocyte/macrophage colony-stimulating factor primes mice for a protective T-cell response" Proc. Natl. Acad. Sci. USA, Oct. 1996, 93:10972-10977.

Lin, K.H. et al. "Regulation of Aldehyde Dehydrogenase Activity in Five Rat Hepatoma Cell Lines" Cancer Res, Nov. 1984, 44:5219-5226.

Lindahl, R. "Aldehyde Dehydrogenases and Their Role in Carcinogenesis" Critical Reviews in Biochemistry and Molecular Biology, 1992, 27(4,5):283-335.

Lioznov, M.V. et al. "Aldehyde dehydrogenase activity as a marker for the quality of hematopoietic stem cell transplants" Bone Marrow Transplantation, 2005, 35:909-914.

Magni, M. et al. "Induction of cyclophosphamide-resistance by aldehyde-dehydrogenase gene transfer" Blood, 1996, 87:1097-1103.

Maki, P.A. et al. "Potentiation of the Cytotoxic Action of Mafosfamide by N-Isopropyl-pformylbenzamide, a Metabolite of Procarbazine" Cancer Research, Aug. 15, 1991, 51:4170-4175.

Moreb, J.S. et al. "Retinoic Acid Down-Regulates Aldehyde Dehydrogenase and Increases Cytotoxicity of 4-Hydroperoxycyclophosphamide and Acetaldehyde" JPET, 2005, 312(1):339-345.

Povsic, T.J. et al. "Circulating Progenitor Cells Can Be Reliably Identified on the Basis of Aldehyde Dehydrogenase Activity" JACC, Dec. 4, 2007, 50(23):2243-2248.

Rekha, G.K. et al. "Multienzyme-mediated stable and transient multidrug resistance and collateral sensitivity induced by xenobiotics" Cancer Chemother Pharmacol, 1997, 40:215-224.

Russo, J.E. et al. "Characterization of Cytosolic Aldehyde Dehydrogenase from Cyclophosphamide Resistant L1210 Cells" Cancer Res, Jun. 1, 1988, 48:2963-2968.

Safety Data Sheet "Cyclophosphamide" Division of Occupational Health and Safety National Institutes of Health, prepared by the Environmental Control and Research Program, Mar. 1987, 8 pages.

Sahovic, E.A. et al. "Role for Aldehyde Dehydrogenase in Survival of Progenitors for Murine Blast Cell Colonies after Treatment with 4-Hydroperoxycyclophosphamide in Vitro" Cancer Research, Mar. 1, 1988, 48:1223-1226.

Shih, W.W.H. et al. "Difference in effect of single immunosuppressive agents (cyclophosphamide, CCNU, 5-FU) on peripheral blood immune cell parameters and central nervous system immunoglobulin synthesis rate in patients with multiple sclerosis" Clin. Exp. Immunol., 1983, 53:122-132.

Sládek, N. E. et al. "Aldehyde Dehydrogenase-Mediated Cellular Relative Insensitivity to the Oxazaphosphorines" Curr. Pharm. Des., 1999, 5(8):607-625.

Sládek, N. E. et al. "Cellular levels of aldehyde dehydrogenases (ALDH1A1 and ALDH3A1) as predictors of therapeutic responses to cyclophosphamide-based chemotherapy of breast cancer: a retrospective study" Cancer Chemother Pharmacol, 2002, 49:309-321.

Sládek, N. E. et al. "Human Aldehyde Dehydrogenases: Potential Pathological, Pharmacological, and Toxicological Impact" J. Biochem. Molecular Toxicology, 2003, 17(1):7-23.

Sreerama, L. et al. "Identification of a Methylcholanthrene-induced Aldehyde Dehydrogenase in a Human Breast Adenocarcinoma Cell Line Exhibiting Oxazaphosphorine-specific Acquired Resistance" Cancer Res, Apr. 15, 1994, 54:2176-2185.

Sreerama, L. et al. "Identification of a Class 3 Aldehyde Dehydrogenase in Human Saliva and Increased Levels of this Enzyme, Glutathione S-Transferases, and DT-Diaphorase in the Saliva of Subjects Who Continually Ingest Large Quantities of Coffee or Broccoli" Clin Cancer Res, Oct. 1995, 1:1153-1163.

Sreerama, L. et al. "Cellular Levels of Class 1 and Class 3 Aldehyde Dehydrogenases and Certain Other Drug-metabolizing Enzymes in Human Breast Malignancies" Clinical Cancer Research, Nov. 1997, 3:1901-1914.

Takebe, N. et al. "Generation of Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene" Molecular Therapy, Jan. 2001, 3(1):88-96.

Venkataranganna, M.V. et al. "Pharmacodynamics & toxicological profile of PartySmart, a herbal preparation for alcohol hangover in Wistar rats" Indian J Med Res, May 2008, 127:460-466.

Zhang, J. et al. "Clinical Pharmacology of Cyclophosphamide and Ifosfamide" Current Drug Therapy, 2006, 1:55-84.

Zoumbos, N.C. et al. "Circulating Activated Suppressor T Lymphocytes in Aplastic Anemia" *The New England Journal of Medicine*, Jan. 31, 1985, 312(5):257-265.

International Search Report dated Jun. 10, 2009 in International Application Serial No. PCT/US2008/084396, filed Nov. 21, 2008.

International Search Report dated Jun. 25, 2009 in International Application Serial No. PCT/US2008/084414, filed Nov. 21, 2008.

\* cited by examiner

METHOD OF IDENTIFYING PATIENTS NOT SUITABLE FOR HIGH-DOSE CYCLOPHOSPHAMIDE TREATMENT

The application is a continuation of application Ser. No. 13/026,590, filed Feb. 14, 2011, now abandoned, which is a continuation of application Ser. No. 12/827,773, filed Jun. 30, 2010, now abandoned, which is a continuation of application Ser. No. 12/610,756, filed Nov. 2, 2009, now abandoned, which is a continuation of application Ser. No. 12/404,900, filed Mar. 16, 2009, now abandoned, which is a continuation of PCT/US07/78518, filed Sep. 14, 2007, which claims benefit of 60/844,829, filed Sep. 15, 2006.

BACKGROUND

Aldehyde dehydrogenases (ALDHs) are intracellular enzymes responsible for oxidizing aldehydes. Substrates for ALDHs include acetyldehyde, an intermediate in ethanol metabolism, and biogenic amines produced during catecholamine catabolism. (Russo et al., *Cancer Res.* 48: 2963-2968 (1988)). ALDH has also been reported to play a crucial role in the conversion of vitamin A to its active metabolite, retinoic acid. (Labrecque et al., *Biochem. Cell Biol.* 71:85-89 (1993); Yoshida et al., *Enzyme* 46:239-244 (1992)).

High enzymatic activity of aldehyde dehydrogenase (ALDH) has been shown to be a characteristic feature of primitive hematopoeitic progenitor cells in mice and humans. (Kohn et al., *Biochem. Pharmacol.* 34:3465-3471 (1985); Kastan et al., *Blood* 75:1947-1950 (1990)). ALDH activity has been previously used as a marker to assess for the quality of hematopoeitic stem cell transplants. (Lioznov et al., *Bone Marrow Transplant.* 35:909-914 (2005)).

A number of studies seem to suggest that ALDH confers resistance of cells to cyclophosphamide, which is routinely used for the treatment of autoimmune diseases and cancer. For example, cyclophosphamide is included in various chemotherapeutic regiments for treatment of cancer and high-dose cyclophosphamide (for example, 50 mg/kg/day×4 days) has been used for the treatment of certain autoimmune diseases such as, for example, severe aplastic anemia. High dose cyclophosphamide therapy appears to be effective than the low-dose therapy which usually requires daily oral dosing or monthly intravenous pulses at 500-1000 mg/m$^2$ and has a higher risk of malignancies and premature menopause and/or infertility. High dose cyclophosphamide therapy, however, is not suitable for all patients, because of higher toxicity.

It also has been observed that in patients receiving high-dose cyclophosphamide therapy for autoimmune diseases, patients who achieved maximal immunosuppression following the therapy as indicated by their white blood cell count (WBC) reaching 0 experience a better clinical outcome and lessened risk of disease relapse than patients whose white blood cell count did not reach zero following therapy.

Analysis of the banked blood of a series of patients following high-dose cyclophosphamide treatment demonstrated that patients who reached a white blood cell count of 0 and subsequently enjoyed a better clinical outcome had much had a much lower level of ALDH activity than the patient who relapsed without reaching a WBC of 0.

The observed outcomes and the ALDH measures obtained from the banked blood samples suggest that treatment success depends on both the ability of hematopoietic stem cells to resist high-dose cyclophosphamide as a result of their elevated ALDH and on a sufficiently weak or absent ALDH level in peripheral lymphocytes which renders those cells sensitive to treatment.

It is generally difficult to predict which patients might be suitable for high-dose cyclophosphamide. It is also generally difficult to predict which patients might experience treatment failure or disease relapse following high-dose cyclophosphamide therapy due to their peripheral lymphocytes being resistant to the administered drug dose.

SUMMARY

The present invention is based, at least in part, on the discovery that an enzyme called aldehyde dehydrogenase (ALDH), which plays an important role in the metabolism of cyclophosphamide, may be used as an indicator for identifying patients that are suitable for high-dose cyclophosphamide treatment. This is especially useful i in determining which patients are likely to most benefit from the administered therapy.

In one aspect, the present invention provides a method for identifying a subject suitable for high-dose cyclophosphamide treatment. The method includes measuring ALDH in a sample including hematopoietic stem cells derived from the subject, where the subject is identified as being suitable for high-dose cyclophosphamide treatment if the ALDH is consistent with a resistant ALDH standard in hematopoietic stem cells.

In another aspect, the present invention provides a method for identifying a subject not suitable for high-dose cyclophosphamide treatment. The method includes measuring ALDH in a sample including hematopoietic stem cells derived from the subject, where the subject is identified as not being suitable for high-dose cyclophosphamide treatment if the ALDH is not consistent with a resistant standard or is consistent with a sensitive ALDH standard in hematopoietic stem cells.

In yet another aspect, the present invention provides a method for identifying a subject suitable for high-dose cyclophosphamide treatment. The method includes measuring ALDH in a sample including peripheral lymphocytes derived from the subject, where the subject is identified as being suitable for high-dose cyclophosphamide treatment if the ALDH is consistent with a sensitive ALDH standard in peripheral lymphocytes.

In another aspect, the present invention provides a method for identifying a subject not suitable for high-dose cyclophosphamide treatment. The method includes measuring ALDH in a sample including peripheral lymphocytes derived from the subject, where the subject is identified as not being suitable for high-dose cyclophosphamide treatment if the ALDH is not consistent with a sensitive or is consistent with a resistant ALDH standard in peripheral lymphocytes.

In one aspect, the present invention provides a method for identifying a subject suitable for high-dose cyclophosphamide treatment. The method includes measuring ALDH in a sample including peripheral lymphocytes derived from the subject, where the subject is identified as being suitable for high-dose cyclophosphamide treatment if the ALDH is consistent with an ALDH standard demonstrated to allow maximal immunosuppression in the subject following administration of high-dose cyclophosphamide.

In yet another aspect, the present invention provides a method for identifying a subject suitable for high-dose cyclophosphamide treatment. The method includes measuring ALDH in a sample including hematopoeitic stem cells derived from a subject, where the subject is identified as being suitable for high-dose cyclophosphamide treatment if the measured ALDH is consistent with an appropriate standard of ALDH. Conversely, a subject is identified as not being suitable for high-dose cyclophosphamide treatment if ALDH is not consistent with an appropriate standard.

In yet another aspect, the present invention provides a method for identifying a subject suitable for high-dose cyclophosphamide treatment. The method includes measuring ALDH in a sample including peripheral lymphocytes derived from a subject, where the subject is identified as being suitable for high-dose cyclophosphamide treatment if ALDH is consistent with an appropriate standard. Conversely, a subject is identified as not being suitable for high-dose cyclophosphamide treatment if ALDH is not consistent with an appropriate standard.

In yet another aspect, the present invention provides a method of determining a dose of cyclophosphamide suitable for administration to a subject. The methods includes: (a) measuring ALDH in a sample including hematopoeitic stem cells derived from the subject; and (b) determining an effective dose of cyclophosphamide based on comparison of ALDH to an appropriate standard.

In yet another aspect, the present invention provides a method of determining a dose of cyclophosphamide suitable for administration to a subject. The methods includes: (a) measuring ALDH in a sample including peripheral lymphocytes derived from the subject; and (b) determining an effective dose of cyclophosphamide based on comparison of ALDH to an appropriate standard.

In yet another aspect, the present invention provides a method of determining a dose of cyclophosphamide suitable for administration to a subject. The methods includes: (a) measuring ALDH in a sample including peripheral lymphocytes derived from the subject; (b) measuring ALDH in a sample including hematopoietic stem cells derived from the subject; and (c) determining an effective dose of cyclophosphamide based on comparison of both ALDH measurements to corresponding appropriate standards.

In some embodiments of the present invention, the subject has an autoimmune disease. Exemplary autoimmune disease include, but are not limited to, AIDS-associated myopathy, AIDS-associated neuropathy, Acute disseminated encephalomyelitis, Addison's Disease, Alopecia Areata, Anaphylaxis Reactions, Ankylosing Spondylitis, Antibody-related Neuropathies, Antiphospholipid Syndrome, Autism, Autoimmune Atherosclerosis, Autoimmune Diabetes Insipidus, Autoimmune Endometriosis, Autoimmune Eye Diseases, Autoimmune Gastritis, Autoimmune Hemolytic Anemia, Autoimmune Hemophilia, Autoimmune Hepatitis, Autoimmune Interstitial Cystitis, Autoimmune Lymphoproliferative Syndrome, Autoimmune Myelopathy, Autoimmune Myocarditis, Autoimmune Neuropathies, Autoimmune Oophoritis, Autoimmune Orchitis, Autoimmune Thrombocytopenia, Autoimmune Thyroid Diseases, Autoimmune Urticaria, Autoimmune Uveitis, Autoimmune Vasculitis, Behcet's Disease, Bell's Palsy, Bullous Pemphigoid, CREST, Celiac Disease, Cerebellar degeneration (paraneoplastic), Chronic Fatigue Syndrome, Chronic Rhinosinusitis, Chronic inflammatory demyelinating polyneuropathy, Churg Strauss Syndrome, Connective Tissue Diseases, Crohn's Disease, Cutaneous Lupus, Dermatitis Herpetiformis, Dermatomyositis, Diabetes Mellitus, Discoid Lupus Erythematosus, Drug-induced Lupus, Endocrine Orbitopathy, Glomerulonephritis, Goodpasture Syndrome, Goodpasture's Syndrome, Graves Disease, Guillian-Barre Syndrome, Miller Fisher variant of the Guillian Barre Syndrome, axonal Guillian Barre Syndrome, demyelinating Guillian Barre Syndrome, Hashimoto Thyroiditis, Herpes Gestationis, Human T-cell lymphomavirus-associated myelopathy, Huntington's Disease, IgA Nephropathy, Immune Thrombocytopenic Purpura, Inclusion body myositis, Interstitial Cystitis, Isaacs syndrome, Lambert Eaton myasthenic syndrome, Limbic encephalitis, Lower motor neuron disease, Lyme Disease, MCTD, Microscopic Polyangiitis, Miller Fisher Syndrome, Mixed Connective Tissue Disease, Mononeuritis multiplex (vasculitis), Multiple Sclerosis, Myasthenia Gravis, Myxedema, Meniere Disease, Neonatal LE, Neuropathies with dysproteinemias, Opsoclonus-myoclonus, PBC, POEMS syndrome, Paraneoplastic Autoimmune Syndromes, Pemphigus, Pemphigus Foliaceus, Pemphigus Vulgaris, Pernicious Anemia, Peyronie's Disease, Plasmacytoma/myeloma neuropathy, Poly-Dermatomyositis, Polyarteritis Nodosa, Polyendocrine Deficiency Syndrome, Polyendocrine Deficiency Syndrome Type 1, Polyendocrine Deficiency Syndrome Type 2, Polyglandular Autoimmune Syndrome Type I, Polyglandular Autoimmune Syndrome Type II, Polyglandular Autoimmune Syndrome Type III, Polymyositis, Primary Biliary Cirrhosis, Primary Glomerulonephritis, Primary Sclerosing Cholangitis, Psoriasis, Psoriatic Arthritis, Rasmussen's Encephalitis, Raynaud's Disease, Relapsing Polychondritis, Retrobulbar neuritis, Rheumatic Diseases, Rheumatoid Arthritis, Scleroderma, Sensory neuropathies (paraneoplastic), Sjogren's Syndrome, Stiff-Person Syndrome, Subacute Thyroiditis, Subacute autonomic neuropathy, Sydenham Chorea, Sympathetic Ophthalmitis, Systemic Lupus Erythematosus, Transverse myelitis, Type 1 Diabetes, Ulcerative Colitis, Vasculitis, Vitiligo, Wegener's Granulomatosis, Acrocyanosis, Anaphylactic reaction, Autoimmune inner ear disease, Bilateral sensorineural hearing loss, Cold agglutinin hemolytic anemia, Cold-induced immune hemolytic anemia, Idiopathic endolymphatic hydrops, Idiopathic progressive bilateral sensorineural hearing loss, Immune-mediated inner ear disease, and Mixed autoimmune hemolysis.

In other embodiments of the present invention, the subject has cancer. Exemplary cancers include, but are not limited to, for example, non-Hodgkin's lymphoma, Hodgkin's lymphoma, chronic lymphocytic leukemia (CLL), mantle cell lymphoma and multiple myeloma. In some embodiments of the methods of the present invention, a sample including hematopoeitic stem cells includes a bone marrow aspirate derived from a subject. In some embodiments of the methods of the present invention a sample including peripheral lymphocytes includes a banked blood sample from the patient.

ALDH can be measured using one of many techniques described herein and those well known in the art. In one embodiment, ALDH is measured using flow cytometry. In another embodiment, ALDH is measured using western blot analysis.

In some embodiments, ALDH is measured using dansyl aminoacetylaldehyde (DAAA) as a substrate. In some other embodiments, ALDH is measured using BODIPY amino acetylaldehyde (BAAA) as a substrate. In some embodiments of the various aspects of the present invention, ALDH is measured by: (a) contacting a sample including hematopoeitic stem cells derived from a subject with DAAA; and (b) measuring oxidation of DAAA.

In some embodiments, ALDH is measured using dansyl aminoacetylaldehyde (DAAA) as a substrate. In some other embodiments, ALDH is measured using BODIPY amino acetylaldehyde (BAAA) as a substrate. In some embodiments of the various aspects of the present invention, ALDH is measured by: (a) contacting a sample including peripheral lymphocytes derived from a subject with DAAA; and (b) measuring oxidation of DAAA.

In some embodiments of the various aspects of the methods of the present invention, a dose of cyclophosphamide used for treating an autoimmune disease or cancer is a non-myeloablative dose. In some embodiments, a dose of cyclophosphamide used for treating an autoimmune disease or cancer is a myeloablative dose, for example, when used in conjunction with stem cell transplantation.

In some embodiments, a non-myeloablative amount of cyclophosphamide used for treating a subject identified using the methods of the invention is between 100 mg/kg and 200 mg/kg, administered daily from 1 to 7 days. In other embodiments, a non-myeloablative amount of cyclophosphamide is between 25 mg/kg and 100 mg/kg, administered daily for 4 consecutive days. In yet other embodiments, a non-myeloablative amount of cyclophosphamide is 50 mg/kg administered daily for 4 consecutive days.

DETAILED DESCRIPTION

This disclosure is based, at least in part, on the discovery that an enzyme called aldehyde dehydrogenase (ALDH) can be used as an indicator for identifying subjects that are suitable for high-dose cyclophosphamide treatment.

High-dose cyclophosphamide was originally used in allogeneic bone marrow transplantation because of its ability to break immune tolerance and facilitate engraftment. (Santos et al., Transplant Proc., 4: 559-564 (1972)).

As a prodrug, cyclophosphamide is converted to 4-hydroxycyclophosphamide (4HC) and its tautomer aldophosphamide in the liver. These compounds diffuse into cells and are converted into the active compound phosphoramide mustard. Alternatively, they are inactivated by the enzyme aldehyde dehydrogenase to form the inert carboxyphosphamide. Lymphoid cells, including NK cells, and B and T lymphocytes, have low levels of aldehyde dehydrogenase and are rapidly killed by high doses (i.e., lymphocytotoxic) of cyclophosphamide. In contrast, hematopoietic progenitor stem cells possess high levels of aldehyde dehydrogenase, rendering them resistant to cyclophosphamide. (Hilton, *Cancer Res.* 44:5156-5160 (1984); Kastan et al., *Blood* 75:1947-1950 (1990); Zoumbos et al., *N. Eng. J. Med.* 312:257-265 (1985); Brodsky, *Sci. World J.* 2:1808-1815 (2002)).

Increased and dependent ALDH activity has been identified as a mechanism of anti-tumor drug resistance to cyclophosphamide. For example, in vivo studies in mice have demonstrated that a cytosolic ALDH isozyme found in murine tumor tissue is responsible for conferring cyclophosphamide resistance. (Russo et al., *Enzyme and Mol. Biol. of Carbonyl Metabolism* 2:65-79 (1989)). Elevated levels of ALDH have also been characterized as being associated with cellular resistance to cyclophosphamide in L1210 murine lymphocytic leukemia model, where a 200-fold higher cytosolic ALDH activity was reported in a cell line resistant to cyclophosphamide when compared to a sensitive cell-line. (DeWys, *J Natl Cancer Inst* 50:783-789(1973)).

Although, ALDH has previously been used for enriching a cell population for hematopoeitic stem cells, the inventors of the present application for the first time recognize that ALDH can also be used for predicting successful outcomes with high dose cyclophosphamide treatment by using it as an indicator in methods for identifying those patients that may be suitable for high-dose cyclophosphamide treatment.

Additionally, ALDH levels in the target peripheral lymphocytes of high-dose cyclophosphamide treatment may render those cells resistant to cyclophosphamide and can lead to worsened clinical outcome or disease relapse. In a series of multiple sclerosis (MS) patients, blood was analyzed to determine the relative levels of aldehyde dehydrogenease. The banked blood was obtained from MS patients prior to treatment with high-dose cyclophosphamide.

Analysis of the banked blood was carried out because it was observed that one MS patient did respond to high-dose cyclophosphamide treatment and one MS patient did not respond to high-dose cyclophosphamide. ALDH measurements were carried out using the banked blood obtained from both of these patients prior to high-dose cyclophosphamide treatment. Analysis of the banked blood from the patient who responded with a zero WBC and the one who did not has given the following preliminary results: the patient that did reach 0 WBC had a much lower level of ALDH activity than the one patient who relapsed after only reaching a nadir WBC of 24 (manuscript in preparation).

The inventors recognize that determining the ALDH level in peripheral lymphocytes from subjects can be used to identifying subjects in whom the resistance of their peripheral lymphocytes to high-dose cyclophosphamide will result in a failure to reach maximal immunosuppression with the supplied cyclophosphamide dose, which in turn increases the possibility of treatment failure or disease relapse in those subjects.

I. Definitions

In order that the present disclosure may be more readily understood, certain terms are first defined. Additional definitions are set forth throughout the detailed description.

As used herein, the term "ALDH" or "aldehyde dehydrogenase" refers to an enzyme or a class of enzymes which are capable of oxidizing aldehydes. Aldehyde dehydrogenase (ALDH) (Enzyme Commission 1.2.1.3) is an enzyme responsible for oxidizing intracellular aldehydes and plays an important role in metabolism of ethanol, vitamin A, and cyclophosphamide. Substrates for ALDH include acetyldehyde and biogenic amines produced during catecholamine catabolism. (Russo et al., *Cancer Res.* 48: 2963-2968 (1988)). ALDH has also been reported to play a crucial role in the conversion of vitamin A to its active metabolite, retinoic acid. (Labrecque et al., *Biochem. Cell Biol.* 71:85-89 (1993); Yoshida et al., *Enzyme* 46:239-244 (1992)).

Four ALDH isoenzymes have been so far identified. (Russo et al., *Cancer Res.* 48:2963-2968 (1988)). Both hematopoeitic progenitors and intestinal crypt stem cells display high levels of cytosolic ALDH and consequently are, relatively resistant to cyclophosphamide. Although, all hematopoeitic progenitors are known to express relatively high levels of cytosolic ALDH, both mouse as well as human hematopoeitic stem cells (HSCs) appear to express even higher levels of ALDH than their less primitive counterparts. Accordingly, primitive hematopoeitic progenitors are generally more resistant to 4HC than later progenitors.

As used herein, the phrase "high dose cyclophosphamide" refers to a lymphocytotoxic, non-myeloablative amount of cyclophosphamide which is immunoablative, upon single or multiple dose administration to a subject (such as a human patient suffering from an autoimmune disease or cancer), thereby resulting in a substantial reduction in or complete elimination of mature circulating lymphocytes in the subject. In some embodiments, administration of a non-myeloablative amount of cyclophosphamide results in treating, preventing, curing, delaying, reducing the severity of, ameliorating at least one symptom of a disorder or recurring disorder, or prolonging the survival of the subject beyond that expected in the absence of such administration. In some embodiments, "a non-myeloablative amount of cyclophosphamide" refers to a dose of cyclophosphamide administered to a subject in need thereof, which results in eliminating or substantially reducing the number of circulating lymphocytes in the subject, including those which are associated with an adverse immune reaction such as, for example, an autoimmune disease, transplant rejection and allergic reaction, or which are associated with cancer, while sparing the hematopoietic progenitor stem cells. For example, in some embodiments, "a non-myeloablative amount of cyclophosphamide" is a 50 mg/kg/day dose of cyclophosphamide administered to a subject in need thereof for 4 consecutive days. Cyclophosphamide is sold under common trade-names including PROCYTOX®, CYTOXAN® and NEOSAR®. As discussed herein, cyclophosphamide is converted to 4-hydroxycyclophosphamide and its tautomer aldophosphamide in the liver and is cytotoxic to cells that express low levels of the enzyme aldehyde dehydrogenase, for example, NK cells and T and B lymphocytes.

The term "resistant ALDH" refers to a level or activity of ALDH which confers resistance of cells to high-dose cyclophosphamide. By resistance to cyclophosphamide is meant that the cells, for example, hematopoeitic stem cells or peripheral lymphocytes having an ALDH level or activity equal to or greater than a "resistant ALDH" survive exposure to high-dose cyclophosphamide. The term "resistant ALDH" also refers to a level or activity of ALDH which is higher than an ALDH level or activity in a cell or cells, for example, a hematopoeitic stem cell or peripheral lymphocyte, which do not survive exposure to high-dose cyclophosphamide.

The terms "non-resistant ALDH" and "sensitive ALDH" in cells refer to the level or activity of ALDH which confers sensitivity or does not confer resistance to high-dose cyclophosphamide. By sensitivity to high-dose cyclophosphamide it is meant that cell or cells, for example, hematopoeitic stem cells or peripheral lymphocytes, having an ALDH level or activity less than "resistant ALDH" are killed by exposure to high-dose cyclophosphamide.

In some embodiments, a subject identified as being suitable for high-dose cyclophosphamide treatment has an ALDH at least 10-fold, or 20-fold, or 30-fold, or 40-fold, or 50-fold or 60-fold, or 70-fold, or 80-fold, or 90-fold, or 100-fold, or 150-fold, or 200-fold, or higher than "resistant ALDH."

In some embodiments, various methodologies of the instant invention include a step that involves comparing ALDH in a sample derived from a subject to a "suitable control," also referred to interchangeably herein as an "appropriate control." A "suitable control" or "appropriate control" is a predetermined value associated with ALDH useful for comparison purposes, which can take many different forms. Exemplary forms include, but are not limited to, for example, a transcription rate, mRNA level, translation rate, protein level, protein structure, biological activity, cellular characteristic or property, genotype, phenotype, enzymatic activity etc. associated with ALDH. In one embodiment, a "suitable control" is a predetermined ALDH activity, which is compared to ALDH activity in a sample derived from a subject being identified as suitable or not suitable for high-dose cyclophosphamide treatment. In another embodiment, a "suitable control" is a predetermined ALDH level, which is compared to ALDH level in a sample derived from a subject being identified as suitable or not suitable for high-dose cyclophosphamide treatment. In another embodiment, a "suitable control" is a predetermined ALDH level, which is compared to ALDH level in a sample derived from a subject in which a clinical measure was achieved, for example an ALDH level obtained from cells in a subject who reached or failed to reach a white blood cell count of 0 following cyclophosphamide treatment.

In some embodiments, a "suitable control" or an "appropriate control" can be a single cut-off value, such as a median or mean. A single cut-off value can be established, for example, based upon comparative groups, such as in groups having an ALDH level or activity which confers resistance to high-dose cyclophosphamide and groups having an ALDH level or activity which does not confer resistance to high-dose cyclophosphamide. For example, hematopoeitic stem cell samples or peripheral lymphocyte samples can be derived from various individuals or blood banks and an ALDH level or activity can be measured in each sample prior to being subjected to high dose cyclophosphamide. Consequently, a single cut-off value can be based on the mean of an ALDH level or activity in samples which are resistant to high dose cyclophosphamide. Another comparative group can be, for example, an ALDH level or activity in a group of individuals with a family history of successful treatment with high-dose cyclophosphamide and a group without such a family history. Another comparative group can be, for example, an ALDH level or activity in a group of individuals with a history of treatment with high-dose cyclophosphamide having achieved maximal immunosuppression and a group having not achieved maximal immunosuppression.

In some embodiments of the methods of the present invention, a subject is identified as being suitable for high-dose cyclophosphamide treatment if the ALDH measured in a hematopoeitic stem cell sample or a peripheral lymphocyte sample derived from the subject is consistent with an "appropriate control." By "consistent with an appropriate control," is meant that the ALDH is either equal to than a predetermined ALDH control, in case of a single cut-off value, or the ALDH falls within a range for a predetermined ALDH control. In some embodiments, a subject is identified as being suitable for high-dose cyclophosphamide treatment if the ALDH measured in a hematopoeitic stem cell sample derived from the subject is consistent with a "resistant ALDH" in hematopoietic stem cells. By "consistent with a resistant ALDH," is meant that the ALDH is either equal to or higher than a predetermined "resistant ALDH," in case of a single cut-off value, or the ALDH falls within a range for a predetermined resistant ALDH. In other embodiments, a subject is identified as being suitable for high-dose cyclophosphamide treatment if the ALDH measured in a peripheral lymphocyte cell derived from the subject is consistent with a "sensitive ALDH" in peripheral lymphocytes. By "consistent with a sensitive ALDH," is meant that the ALDH is either equal to or lower than a predetermined "sensitive ALDH," in case of a single cut-off value, or the ALDH falls within a range for a predetermined sensitive ALDH.

The terms "treat," "treating," and "treatment," as used herein, refer to therapeutic or preventative measures described herein. The methods of "treatment" employ administration to a subject identified using methods of the present invention, for example, a subject having an autoimmune disease, an allergic reaction, transplant rejection, or cancer, or who ultimately may acquire a disorder such as, for example, an autoimmune disease, an allergic reaction, transplant rejection, or cancer, a lymphocytotoxic non-myeloablative amount of cyclophosphamide, in order to prevent, cure, delay, reduce the severity of, or ameliorate one or more symptoms of the disorder or recurring disorder, or in order to prolong the survival of a subject beyond that expected in the absence of such treatment.

The terms "cure" and "curing," as used herein, refer to a complete remission of a disease in a subject identified using the methods of the present invention, such as, for example, a subject having an autoimmune disease, an allergic reaction, transplant rejection, or cancer, by the administration of a lymphocytotoxic non-myeloablative amount of cyclophosphamide to the subject.

The term "hematopoietic progenitor stem cell," as used herein refers to any type of cell of the hematopoietic system, including, but not limited to, undifferentiated cells such as hematopoietic stem cells and progenitor cells, which are capable of reconstituting the immune system following administration of a lymphocytotoxic non-myeloablative amount of cyclophosphamide to a subject identified using the methods described herein.

The terms "peripheral lymphocyte", "differentiated lymphocyte", and "mature lymphocyte", as used interchangeably herein, refer to the immune system cells which are differentiated and distinct from the hematopoietic progenitor stem cells. These can include populations or individual cells of circulating differentiated lymphocytes (e.g., NK cells, and T and B lymphocytes).

The terms "immunoablation" and "immunoablative," as used herein, refer to severe immunosuppression using a high-dose (i.e., lymphocytotoxic non-myeloablative amount) of cyclophosphamide, for example, 50 mg/kg×4 days of cyclophosphamide, which leads to substantial reduction in or elimination of the population of circulating lymphocytes, including for example, NK cells and B and T lymphocytes Immunoablation, as described herein, results in complete or substantially complete reduction in autoreactive antibodies and memory cells responsible for an autoimmune response.

The term "lymphocytotoxic," as used herein, refers to complete elimination of or substantial reduction in the number of circulating lymphocytes, including those associated with an adverse immune reaction in a subject, such as, for example, an autoimmune disease, an allergic reaction, a transplant rejection, or cancer in a subject following administration of a high-dose (i.e., lymphocytotoxic non-myeloablative amount) of cyclophosphamide, such as, for example, 50 mg/kg×4 days of cyclophosphamide.

The term "non-myeloablative," as used herein, refers to a property of a compound such as, for example, cyclophosphamide, whereby the compound does not have a cytotoxic effect on myeloid cells, for example, hematopoietic progenitor stem cells. In some embodiments, a non-myeloablative agent used in the methods described herein has a cytotoxic effect on the circulating mature lymphocytes (e.g., NK cells, and T and B lymphocytes) while sparing the progenitor cells, e.g., hematopoietic progenitor stem cells that are capable of reconstituting the immune system. In some embodiments, a non-myeloablative agent used in the methods of the invention kills cells which express low or sensitive levels of the enzyme aldehyde dehydrogenase (e.g., NK cells and B and T lymphocytes) while sparing cells which express high or resistant levels of the enzyme aldehyde dehydrogenase (e.g., hematopoietic progenitor stem cells).

The term "maximally immunosuppressive," or "maximal immunosuppression" as used herein, refers to a treatment which eliminates or reduces the mature lymphocytes of a patient but does not have a cytotoxic effect on myeloid cells, for example, hematopoietic progenitor stem cells. The treatment has a cytotoxic effect on the circulating mature lymphocytes (e.g., NK cells, and T and B lymphocytes) while sparing the progenitor cells, e.g., hematopoietic progenitor stem cells that are capable of reconstituting the immune system. In some embodiments, a maximally immunosuppressive agent used in the methods of the invention kills cells which express low or sensitive levels of the enzyme aldehyde dehydrogenase (e.g., NK cells and B and T lymphocytes) while sparing cells which express high or resistant levels of the enzyme aldehyde dehydrogenase (e.g., hematopoietic progenitor stem cells).

II. Subjects Being Identified

Various methods described herein can be used for identifying a subject as being suitable or not being suitable for high-dose cyclophosphamide treatment, where the subject has an autoimmune disease, an allergic reaction, transplant rejection or cancer.

In one embodiment, a subject being identified as being suitable or not being suitable for high-dose cyclophosphamide treatment has an autoimmune disease. Exemplary autoimmune diseases include, but are not limited to, AIDS-associated myopathy, AIDS-associated neuropathy, Acute disseminated encephalomyelitis, Addison's Disease, Alopecia Areata, Anaphylaxis Reactions, Ankylosing Spondylitis, Antibody-related Neuropathies, Antiphospholipid Syndrome, Autism, Autoimmune Atherosclerosis, Autoimmune Diabetes Insipidus, Autoimmune Endometriosis, Autoimmune Eye Diseases, Autoimmune Gastritis, Autoimmune Hemolytic Anemia, Autoimmune Hemophilia, Autoimmune Hepatitis, Autoimmune Interstitial Cystitis, Autoimmune Lymphoproliferative Syndrome, Autoimmune Myelopathy, Autoimmune Myocarditis, Autoimmune Neuropathies, Autoimmune Oophoritis, Autoimmune Orchitis, Autoimmune Thrombocytopenia, Autoimmune Thyroid Diseases, Autoimmune Urticaria, Autoimmune Uveitis, Autoimmune Vasculitis, Behcet's Disease, Bell's Palsy, Bullous Pemphigoid, CREST, Celiac Disease, Cerebellar degeneration (paraneoplastic), Chronic Fatigue Syndrome, Chronic Rhinosinusitis, Chronic inflammatory demyelinating polyneuropathy, Churg Strauss Syndrome, Connective Tissue Diseases, Crohn's Disease, Cutaneous Lupus, Dermatitis Herpetiformis, Dermatomyositis, Diabetes Mellitus, Discoid Lupus Erythematosus, Drug-induced Lupus, Endocrine Orbitopathy, Glomerulonephritis, Goodpasture Syndrome, Goodpasture's Syndrome, Graves Disease, Guillain-Barre Syndrome, Guillian Barre Syndrome (Miller Fisher variant), Guillian Barre Syndrome (axonal), Guillian Barre Syndrome (demyelinating), Hashimoto's Thyroiditis, Herpes Gestationis, Human T-cell lymphomavirus-associated myelopathy, Huntington's Disease, IgA Nephropathy, Immune Thrombocytopenic Purpura, Inclusion body myositis, Interstitial Cystitis, Isaacs syndrome, Lambert Eaton myasthenic syndrome, Limbic encephalitis, Lower motor neuron disease, Lyme Disease, MCTD, Microscopic Polyangiitis, Miller Fisher Syndrome, Mixed Connective Tissue Disease, Mononeuritis multiplex (vasculitis), Multiple Sclerosis, Myasthenia Gravis, Myxedema, Meniere Disease, Neonatal LE, Neuropathies with dysproteinemias, Opsoclonus-myoclonus, PBC, POEMS syndrome, Paraneoplastic Autoimmune Syndromes, Pemphigus, Pemphigus Foliaceus, Pemphigus Vulgaris, Pernicious Anemia, Peyronie's Disease, Plasmacytoma/myeloma neuropathy, Poly-Dermatomyositis, Polyarteritis Nodosa, Polyendocrine Deficiency Syndrome, Polyendocrine Deficiency Syndrome Type 1, Polyendocrine Deficiency Syndrome Type 2, Polyglandular Autoimmune Syndrome Type I, Polyglandular Autoimmune Syndrome Type II, Polyglandular Autoimmune Syndrome Type III, Polymyositis, Primary Biliary Cirrhosis, Primary Glomerulonephritis, Primary Sclerosing Cholangitis, Psoriasis, Psoriatic Arthritis, Rasmussen's Encephalitis, Raynaud's Disease, Relapsing Polychondritis, Retrobulbar neuritis, Rheumatic Diseases, Rheumatoid Arthritis, Scleroderma, Sensory neuropathies (paraneoplastic), Sjogren's Syndrome, Stiff-Person Syndrome, Subacute Thyroiditis, Subacute autonomic neuropathy, Sydenham Chorea, Sympathetic Ophthalmitis, Systemic Lupus Erythematosus, Transverse myelitis, Type 1 Diabetes, Ulcerative Colitis, Vasculitis, Vitiligo, Wegener's Granulomatosis, Acrocyanosis, Anaphylactic reaction, Autoimmune inner ear disease, Bilateral sensorineural hearing loss, Cold agglutinin hemolytic anemia, Cold-induced immune hemolytic anemia, Idiopathic endolymphatic hydrops, Idiopathic progressive bilateral sensorineural hearing loss, Immune-mediated inner ear disease, and Mixed autoimmune hemolysis.

Without wishing to be bound by theory, it is understood that methods described herein can be used for identifying a subject suitable for high-dose cyclophosphamide treatment, where the subject has any immune disorder in which it would be desirable to replace the circulating auto-reactive lymphocytes with disease free immune cells. One of ordinary skill in the art can easily determine which diseases fall in this category, for example, by detecting auto-reactive antibodies or antibodies which react with self-antigens in a subject suffering from such a disease. Alternatively, by detecting cells in a subject which are capable of mounting an immune response against a self-antigen in the subject. Methods of diagnosing one or more autoimmune diseases encompassed by this disclosure are well-known in the art and can easily be performed by a skilled artisan.

In addition to autoimmune diseases, also encompassed by this invention are methods of identifying subjects suitable for high-dose cyclophosphamide treatment, where the subject has an allergic reaction. Exemplary allergic reactions include, but are not limited to, systemic allergic reaction, an allergic reaction to immunotherapy, anaphylactic reaction, atopic disease, contrast allergy, drug allergy, food allergy, hypersensitivity reaction, insect sting allergy, latex allergy, penicillin allergy, and radiocontrast medium allergy. Examples of food allergies include an allergic reaction to peanuts or shellfish, for example.

In addition to autoimmune diseases and allergic reactions, also encompassed by the methods of the present invention are methods of identifying subjects having transplant rejections as being suitable or not being suitable for high-dose cyclophosphamide treatment. For example, in some embodiments, a subject has a transplant rejection which occurred during or following an allogenic antigen transplantation of organs, tissues, or cells into a host. In other embodiments, a subject has a transplant rejection which occurred during or following a xenogenic transplantation of organs, tissues, or cells into a host. In yet other embodiments, a subject has a transplant rejection which occurred during or following transplantation of autologous tissue, organs or cells into a host.

Also encompassed by the methods of the present invention are subjects which have a transplant rejection that occurred during or following a transplant of an organ, tissue or cells from a half-matched donor, which usually results in graft versus host disease.

In a further embodiment of the present invention, a subject has cancer. As used herein, the term "cancer" refers to disorders characterized by deregulated or uncontrolled cell growth, for example, carcinomas, sarcomas, lymphomas. The term "cancer" includes benign tumors, primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

Exemplary cancers include, but are not limited to, Hodgkin's Lymphoma, Non-Hodgkin's Lymphoma, Chronic Lymphocytic Leukemia, Mantle Cell Lymphoma and Multiple Myeloma.

III. Preparation of Cell Sample Containing Hematopoeitic Stem Cells

In various aspects of the methods of the invention, ALDH, for example, cytosolic ALDH, is measured in a cell sample including hematopoietic stem cells, for example, a cell suspension of pluripotent hematopoietic stem cells (pluripotent HSC), that is substantially free of lineage-committed cells. By definition, "pluripotent" hematopoietic stem cells are those progenitor cells having the ability to repopulate lymphohematopoietic lineages on a long-term basis.

In one embodiment, hematopoeitic stem cells are derived from a subject having an autoimmune disease. In another embodiment, hematopoeitic stem cells are derived from a subject having cancer. In yet other embodiments, a subject has an allergic reaction or transplant rejection.

Preparation of cell samples containing hematopoeitic stem cells can be found, for example, in U.S. Pat. No. 5,876,956, incorporated by reference herein, in its entirety. Alternatively, a large proportion of differentiated cells may be removed in a cell sample by using, for example, a "relatively crude" separation. The source of the cells may be the bone marrow, fetal, neonate, or adult or other hematopoietic cell source, e.g., fetal liver or blood. For example, magnetic bead separations may be used initially to remove large numbers of lineage committed cells, namely major cell populations of the hematopoietic systems, including such lineages as T cells, B cells (both pre-B and B cells), myelomonocytic cells, or minor cell populations, such as megakaryocytes, mast cells, eosinophils and basophils.

In some embodiments, ALDH is measured in a sample derived from a subject having cancer, where the sample contains leukemia cells or other malignant cells.

In some embodiments, a sample derived from a subject includes a substantially homogeneous population of hematopoeitic stem cells. The term "substantially homogeneous," as used herein, means that the sample derived from a subject being identified as being suitable or not suitable for high-dose cyclophosphamide treatment includes no more than about 1%, or 2%, or 5%, or 10% of lineage-committed cells. Hematopoeitic stem cells can be isolated using any technique well-known in the art or those described herein. For example, hematopoeitic stem cells can be characterized as having one or more of the following attributes, for example, having a small size, generally from about 8 to 10 µm; expressing levels of ALDH from about 10 to about 30 nanomoles aldehyde oxidized/mg protein/min; being substantially free from expression of markers specific for committed lymphohematopoietic lineages, such as CD19, CD33 and CD5; and being negative for expression of c-kit and Thy. In some embodiments, a sample derived from a subject is enriched for hematopoeitic stem cells, for example, by flow cytometry using anti-CD34 antibody. Other markers that can be used for identification and isolation of hematopoeitic stem cells include, but are not limited to, c-kit and Thy.

In some embodiments, a cell sample including hematopoietic stem cells can be obtained by isolating cells that express an intracellular enzyme which hydrolyzes a fluorescent nonpolar substrate. Preferably, the enzyme is ALDH and the substrate is DAAA as described herein. In other embodiments, the cell sorting step is performed using automated cell sorting, such as fluorescence activated cell sorting (FACS), a high speed method of sorting fluorescent cells.

Preparation of Cell Sample Containing Peripheral Lymphocytes

In various aspects of the methods of the invention, ALDH, for example, cytosolic ALDH, is measured in a cell sample including peripheral lymphocytes, for example, a cell suspension substantially enriched of lineage-committed immune cells. By definition, these lymphocytes originate from a common lymphoid progenitor and form the innate and humoral immune system. These cells are commonly referred to as T cells, B cells and natural killer (NK) cells, white blood cell, and/or dendritic cells. These include such lineages as T cells, B cells (both pre-B and B cells), myelomonocytic cells, or minor cell populations, such as megakaryocytes, mast cells, eosinophils and basophils.

In one embodiment, peripheral lymphocytes are derived from a subject having an autoimmune disease. In another embodiment, peripheral lymphocytes cells are derived from a subject having cancer. In yet other embodiments, a subject has an allergic reaction or transplant rejection.

Preparation of cell samples enriched in peripheral lymphocytes can be obtained using known methods in the art including flow cytometry The source of the cells may be the bone marrow, fetal, neonate, or adult or other hematopoietic cell source, e.g., fetal liver or blood. For example, magnetic bead separations may be used initially to remove large numbers of lineage committed cells, namely major cell populations of the hematopoietic systems, including such lineages as T cells, B cells (both pre-B and B cells), myelomonocytic cells, or minor cell populations, such as megakaryocytes, mast cells, eosinophils and basophils.

In some embodiments, ALDH is measured in a sample derived from a subject having cancer, where the sample contains leukemia cells or other malignant cells.

In some embodiments, a sample derived from a subject includes a substantially homogeneous population of peripheral lymphocytes. The term "substantially homogeneous," as used herein, means that the sample derived from a subject being identified as being suitable or not suitable for high-dose cyclophosphamide treatment includes more than about 1%, or 2%, or 5%, or 10% of lineage-committed cells. Hematopoeitic stem cells can be isolated using any technique well-known in the art or those described herein. For example, peripheral lymphocyes can be characterized as having one or more of the following attributes, for example expression of markers specific for committed lymphohematopoietic lineages, such as CD19, CD33 and CD5; or being positive for expression of c-kit and Thy.

IV. Measurement of ALDH

Various methods known in the art and those described herein can be used for measuring ALDH in a cell sample including hematopoeitic stem cells or peripheral lymphocytes.

In some embodiments, ALDH activity is measured using a fluorescent substrate called dansyl-aminoacetaldehyde or DAAA, as a substrate. In another exemplary method, ALDH activity is measured using boron-dipyrromethene (BODIPY) aminoacetaldehyde or BAAA as a substrate (commercially available as ALDEFLUOR™).

In some embodiments, measurement of ALDH includes the steps of contacting a cell sample containing hematopoeitic stem cells or peripheral lymphocytes with a cell-permeable, non-polar fluorescent aldehyde that is rendered polar by contact with ALDH, for example, by oxidation. Once rendered polar, the fluorescent aldehyde is no longer permeable to the cell membrane and, hence, is trapped within only those cells in the cell mixture that express the intracellular marker. Cells containing the trapped polar, non-permeable fluorescent aldehyde so formed are identified by fluorescence using techniques and equipment well known to those of skill in the art. Exemplary fluorescence techniques include, but are not limited to, automated fluorescence cell sorting techniques that separate cells containing or having attached thereto a fluorescent marker, such as Fluorescence Activated Cell Sorting (FACS). Such fluorescence cell sorting techniques are well known to those of skill in that art.

In some embodiments, a fluorescent cell permeable aldehyde is a substrate for aldehyde dehydrogenase (ALDH), and is oxidized by contact with intracellular ALDH to a non-permeable polar fluorescent molecule. When the fluorescent polar molecule is contacted by a light beam having the requisite wavelength to excite the molecule, the fluorescent light emitted as the molecule drops back to its ground state is detected, thereby indicating the presence of a cell or cell population containing intracellular ALDH. In some embodiments, the fluorescent aldehyde is dansylaminoacetaldehyde (DAAA), a substrate for aldehyde dehydrogenase, or analogs thereof. Dansyl fluorescence is excited at both 351.1 nm and 363.8 nm and is detected at about 521 nm. Description of the synthesis of DAAA can be found in U.S. Pat. No. 5,876,956, incorporated by reference herein, in its entirety.

A general method for producing a non-polar fluorescent aldehyde for measuring ALDH is to react a physiologically compatible fluorescent molecule bearing an electrophilic group and a protected aldehyde, such as a methyl or ethyl acetal having a nucleophilic group. For example, the fluorescent electrophile may be a sulfonyl chloride, such as dansyl chloride or Texas Red sulfonyl chloride; an isothiocyanate, such as fluorescein isothiocyantate; an N-hydroxysuccinimide, such as N-hydroxy succinimidorhodamine; or a thiol-reactive fluorescent derivative, such as 5-iodoacetamidofluorescein. The protected aldehyde may contain one of a number of nucleophilic groups, such as an amino, hydroxyl, phenolic, or thiol group.

Without wishing to be bound by theory, it is contemplated that, any suitable characteristic associated with ALDH such as, for example, mRNA level, polypeptide amount, ALDH activity, transcription rate, translation rate etc., may be used as an indicator for identifying subjects that are suitable for high-dose cyclophosphamide treatment. In some embodiments, ALDH level, for example, amount of ALDH polypeptide present is used as an indicator for identifying subjects suitable for high-dose cyclophosphamide treatment. In other embodiments, ALDH activity is used as an indicator for identifying subjects suitable for high-dose cyclophosphamide treatment.

V. Identification of a Subject Suitable for High-Dose Cyclophosphamide Treatment Subsequent to measuring ALDH in a sample containing hematopoeitic stem cells and/or peripheral lymphocytes derived from a subject, the subject is identified as being suitable or not being suitable for high-dose cyclophosphamide treatment, by for example, comparing the ALDH to a predetermined value.

In some embodiments, a predetermined value is a resistant ALDH, as described herein. Accordingly, in some embodiments, a subject is identified as being suitable for high-dose cyclophosphamide treatment, if the ALDH (e.g., level or activity of ALDH) in a sample including hematopoeitic stem cells derived from the subject is consistent with a resistant ALDH. A resistant ALDH is an ALDH (e.g., level or activity of ALDH) which is sufficient to confer resistance of a hematopoietic stem cell to high-dose cyclophosphamide. In other words, a resistant ALDH is that level or activity of ALDH in a hematopoeitic stem cell or a sample containing hematopoeitic stem cells, at which the cell or cells survive exposure to high-dose cyclophosphamide. In other embodiments, a subject is identified as not being suitable for high-dose cyclophosphamide treatment if the ALDH (e.g., level or activity) is not consistent with a resistant ALDH, or if it is consistent with a sensitive ALDH for the stem cells.

It is understood that a resistant ALDH can be a single value or a range of ALDH which is sufficient for conferring resistance to high-dose cyclophosphamide. For example, in one embodiment, a resistant ALDH is a level of ALDH protein in a sample containing hematopoeitic stem cells which survive exposure to one or more doses of high-dose cyclophosphamide. In another embodiment, a resistant ALDH is an activity of ALDH in a sample containing hematopoeitic stem cells which survive exposure to one or more doses of high-dose cyclophosphamide.

It is understood that a resistant ALDH may either be a value known to one of ordinary skill in the art or it may be determined prior to measuring ALDH in a sample derived from a subject being identified as being suitable or not suitable for high-dose cyclophosphamide treatment.

For example, in some embodiments, a predetermined or resistant ALDH is at least 10 to about 30 nanomoles aldehyde oxidized/mg protein/min. Accordingly, in some embodiments, a subject having ALDH at least 10 to about 30 nanomoles aldehyde oxidized/mg protein/min, or higher, is identified as being suitable for high-dose cyclophosphamide treatment.

In some embodiments, a predetermined ALDH is determined, for example, by expressing varying amounts of ALDH in cells, for example, in cell culture, and exposing them to one or more doses of high-dose cyclophosphamide. Accordingly, a resistant ALDH is the amount or activity of ALDH at which the cells are resistant to high-dose cyclophosphamide. ALDH in a sample derived from a subject being identified using the methods of the invention can subsequently be compared with the resistant ALDH to determine whether the subject is suitable or not suitable for high-dose cyclophosphamide treatment.

In some embodiments according to the present invention, a subject is identified as being suitable or not being suitable for high-dose cyclophosphamide treatment based on the ALDH relative to an appropriate control.

For example, in some embodiments, a subject is identified as being suitable for high-dose cyclophosphamide if a sample containing hematopoeitic stem cells derived from the subject includes an ALDH (e.g., level or activity) which is consistent with appropriate control (i.e., equal or higher than the control in case of a single cut-off value or falling within the appropriate range). Conversely, a subject is identified as not being suitable for high-dose cyclophosphamide treatment if the ALDH (e.g., level or activity) in a sample containing hematopoeitic stem cells derived from the subject is not consistent with an appropriate control (i.e., lower than the control in case of a single cut-off value or not falling within the appropriate range).

It is understood that an appropriate control could be a single value or a range of ALDH which is known to confer resistance to high-dose cyclophosphamide. An appropriate control known in the art may be used in the methods of the invention or it may be determined using one or more methods described herein and those that are known in the art.

For example, in one embodiment, an appropriate control is determined based on the response of a population of subjects to high-dose cyclophosphamide. In some embodiments, a number of samples containing hematopoeitic stem cells are derived from a population of subjects (for example, at least 10, or at least 15, or at least 20, or at least 30, or at least 40, or at least 50, or at least 100, or more). Accordingly, ALDH (e.g., level or activity) can be measured in various samples prior to treatment with high-dose cyclophosphamide. An appropriate control can subsequently be determined as that ALDH (e.g., level or activity) sufficient for conferring resistance to high-dose cyclophosphamide. In other words, an appropriate control can be a single value (e.g., mean or median of ALDH level or activity) or a range of ALDH level or activity in the samples, at which the hematopoeitic stem cells survive exposure to high-dose cyclophosphamide (i.e., resistant ALDH). Accordingly, a subject is subsequently identified as being suitable for high-dose cyclophosphamide treatment if a sample containing hematopoeitic stem cells derived from the subject includes an ALDH (e.g., level or activity) which is consistent with (i.e., at least equal to or higher than) the appropriate control. Conversely, the subject is identified as not being suitable for high-dose cyclophosphamide treatment if the ALDH (e.g., level or activity) is lower than the appropriate control.

Also contemplated by the present invention are methods for determining an effective dose of high-dose cyclophosphamide for administration to a subject. For example, a sample including hematopoeitic stem cells, for example, a bone marrow aspirate, can be derived from a subject and exposed to increasing amounts of cyclophosphamide. A dose of cyclophosphamide can be identified as being suitable for administration to the subject, if hematopoeitic stem cells survive when exposed to the dose, however, are killed when exposed to a dose higher than the dose at which they survive. Accordingly, such a dose is identified as an effective dose for the particular subject.

Also contemplated by the present invention are methods for determining an effective dose of high-dose cyclophosphamide for administration to a subject. For example, a sample including peripheral lymphocytes, for example, a banked blood sample, can be derived from a subject and exposed to increasing amounts of cyclophosphamide. A dose of cyclophosphamide can be identified as being suitable for administration to the subject, if the peripheral lymphocytes are killed when exposed to a dose higher than the dose at which they survive. Another example is a dose within a concentration between which a hematopoietic cell population isolated in a sample survives the treatment and the minimal dose required to kill all or a substantial fraction of the peripheral lymphocytes in a banked blood sample.

Also contemplated by the present invention are methods for determining an effective dose of high-dose cyclophosphamide for administration to a subject. For example, a sample including peripheral lymphocytes, for example, a banked blood sample, can be derived from a subject and exposed to increasing amounts of cyclophosphamide. A dose of cyclophosphamide can be identified as being suitable for administration to the subject, if the dose is within a previously determined range deemed sufficient to drive the subject's white blood cell count to 0 following administration of the therapy. This determination could for instance come from a sampling of the lymphocytes of a similar patient population as the subject or for family members of the subject or from a previous sampling from the patient, or from a model or proxy of the metabolism of the drug by the aldehyde dehydrogenase in the subject.

Accordingly, such a dose is identified as an effective dose for the particular subject.

The specification is most thoroughly understood in light of the teachings of the references cited within the specification which are hereby incorporated by reference. The embodiments within the specification provide an illustration of embodiments in this application and should not be construed to limit its scope. The skilled artisan readily recognizes that many other embodiments are encompassed by this disclosure.

All publications and patents cited and sequences identified by accession or database reference numbers in this disclosure are incorporated by reference in their entirety. To the extent that the material incorporated by reference contradicts or is inconsistent with the present specification, the present specification will supersede any such material. The citation of any references herein is not an admission that such references are prior art to the present specification.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a subject suitable for high-dose cyclophosphamide treatment, comprising measuring the amount or activity of aldehyde dehydrogenase (ALDH) from peripheral lymphocytes from a sample from said subject, wherein the subject is identified as being suitable for high-dose cyclophosphamide treatment if the amount or activity of ALDH is less than the amount or activity of ALDH which confers resistance of the peripheral lymphocytes to high-dose cyclophosphamide treatment, and administering cyclophosphamide to the subject.

2. The method of claim 1, wherein the high-dose cyclophosphamide treatment is used to treat an autoimmune disease.

3. The method of claim 1, wherein the high-dose cyclophosphamide treatment is used to treat cancer.

4. The method of claim 1, wherein the sample comprises a bone marrow aspirate.

5. The method of claim 1, wherein the sample comprises banked blood.

6. The method of claim 1, wherein the amount or activity of ALDH is measured using flow cytometry.

7. The method of claim 1, wherein the amount or activity of ALDH is measured using western blot analysis.

8. The method of claim 1, wherein the amount or activity of ALDH is measured using dansyl aminoacetaldehyde (DAAA) as a substrate.

9. The method of claim 1, wherein the amount or activity of ALDH is measured using boron-dipyrromethene (BODIPY) aminoacetaldehyde (BAAA) as a substrate.

10. The method of claim 1, wherein the amount or activity of ALDH is measured using a substrate for ALDH that yields a fluorescent molecule which is detected using flow cytometry.

* * * * *